(12) United States Patent
Kim

(10) Patent No.: US 11,931,691 B2
(45) Date of Patent: Mar. 19, 2024

(54) POSITIVE PRESSURE AND NEGATIVE PRESSURE MAINTENANCE SYSTEM HAVING BACTERIA STERILIZING FUNCTION AND HARMFUL MATERIAL AND RADIOACTIVE MATERIAL REMOVING FUNCTION

(71) Applicant: Bu Yeol Kim, Ansan-si (KR)

(72) Inventor: Bu Yeol Kim, Ansan-si (KR)

( * ) Notice: Subject to any disclaimer, the term of this patent is extended or adjusted under 35 U.S.C. 154(b) by 721 days.

(21) Appl. No.: 17/051,417

(22) PCT Filed: Apr. 25, 2019

(86) PCT No.: PCT/KR2019/004976
§ 371 (c)(1),
(2) Date: Oct. 28, 2020

(87) PCT Pub. No.: WO2019/212191
PCT Pub. Date: Nov. 7, 2019

(65) Prior Publication Data
US 2021/0093997 A1   Apr. 1, 2021

(30) Foreign Application Priority Data

May 3, 2018   (KR) .................. 10-2018-0051404
Jun. 18, 2018 (KR) .................. 10-2018-0069376

(51) Int. Cl.
*B01D 53/32* (2006.01)
*A61L 9/014* (2006.01)
(Continued)

(52) U.S. Cl.
CPC ............ *B01D 53/323* (2013.01); *A61L 9/014* (2013.01); *A61L 9/22* (2013.01); *B01D 53/0407* (2013.01); *B01D 53/266* (2013.01); *B01D 53/346* (2013.01); *B01D 53/68* (2013.01); *B01D 53/76* (2013.01); *B03C 3/019* (2013.01); *B03C 3/025* (2013.01); *B03C 3/368* (2013.01); *B03C 3/68* (2013.01); *A61L 2209/111* (2013.01);
(Continued)

(58) Field of Classification Search
CPC combination set(s) only.
See application file for complete search history.

(56) References Cited

U.S. PATENT DOCUMENTS

| 2010/0028216 A1 | 2/2010 | Park |
| 2013/0085609 A1 | 4/2013 | Barker |
| 2016/0010231 A1 | 1/2016 | Kim |

FOREIGN PATENT DOCUMENTS

| JP | 3410389 B2 | 5/2003 |
| KR | 10-0803074 B1 | 2/2008 |

(Continued)

*Primary Examiner* — Lessanework Seifu
(74) *Attorney, Agent, or Firm* — Maschoff Brennan

(57) ABSTRACT

The present invention removes, by a preprocessing unit, harmful chemical materials and radioactive materials supplied to a positive pressure chamber and a negative pressure chamber and supplies same, removes contaminants discharged to the outside from the negative pressure chamber and sterilizes bacteria and floating viruses and discharges same, and adjusts, by a control circuit of a control panel, the rotating speed (RPM) of an air supply/discharge fan and adjusts the opening rate of an electric damper according to data that is measured in a pressure sensor provided in a space in which the positive pressure and the negative pressure are to be maintained and is transmitted in real time.

16 Claims, 9 Drawing Sheets

(51) Int. Cl.
*A61L 9/22* (2006.01)
*B01D 53/04* (2006.01)
*B01D 53/26* (2006.01)
*B01D 53/34* (2006.01)
*B01D 53/68* (2006.01)
*B01D 53/76* (2006.01)
*B03C 3/019* (2006.01)
*B03C 3/02* (2006.01)
*B03C 3/36* (2006.01)
*B03C 3/68* (2006.01)

(52) U.S. Cl.
CPC ....... *A61L 2209/14* (2013.01); *A61L 2209/22* (2013.01); *B01D 2253/102* (2013.01); *B01D 2257/2047* (2013.01); *B01D 2257/91* (2013.01); *B01D 2259/4583* (2013.01); *B01D 2259/818* (2013.01)

(56) References Cited

FOREIGN PATENT DOCUMENTS

| KR | 20-2009-005625 U | 6/2009 |
| KR | 10-1101356 B1 | 1/2012 |
| KR | 10-2012-0036214 A | 4/2012 |
| KR | 10-1308788 B1 | 9/2013 |
| KR | 10-2014-0069306 A | 6/2014 |
| KR | 10-1649600 B1 | 8/2016 |
| KR | 10-1701172 B1 | 2/2017 |
| KR | 10-1725258 B1 | 4/2017 |
| KR | 10-2017-0133656 A | 12/2017 |
| WO | 2013/049297 A2 | 4/2013 |

POSITIVE PRESSURE AND NEGATIVE PRESSURE MAINTENANCE SYSTEM HAVING BACTERIA STERILIZING FUNCTION AND HARMFUL MATERIAL AND RADIOACTIVE MATERIAL REMOVING FUNCTION

TECHNICAL FIELD

The present invention relates to a positive pressure and negative pressure maintenance system having a bacteria sterilizing function and a harmful material and radioactive material removing function and, more particularly, to a system which can be utilized in a substation room, a switchboard and a control room of a place involved in handling of spontaneous combustible materials, handling of flammable liquid vapors or flammable gases, and having a risk of fire or explosion due to dust, an operating room and a negative pressure hospital room which gives a medical treatment while placing patients with contagious disease including those infected with or suspicious of the same under quarantine, a clean room of pharmaceutical and food sectors in which cross-contamination is to be prevented, a special-purpose vehicle, emergency operating facilities (EOF) of industrial facilities related to nuclear power, etc.

BACKGROUND ART

As is well known, with the development of the heavy chemical industry in industrialization, various materials such as flammable materials, combustible gases, powdery materials, etc. are used in a manufacturing process, and these materials have a very high chance (frequency) to cause a fire and explosion caused by overheating, runaway reaction and leakage due to careless handling of raw materials and an abnormal process reaction during a product manufacturing process. In case of emergency such as leakage of flammable gases and harmful materials, fire, etc., caused by process abnormality, it is required that a substation room and a control panel stop a troubled process and take a measure to recover the process to a normal state, while an operator controls a related process until the emergency is over in order to minimize any human and physical losses. Thus, it is very important to maintain a positive pressure in terms of ensuring safety in the substation room, etc., from the inflow of combustible gases, toxic gases, and flames from the outside. In the pharmaceutical industry, products are classified into tablets, capsules, ointments, injections, etc., and a degree of cleanliness for each formulation (fine dust, falling bacteria, temperature, humidity, positive pressure and negative pressure management, etc.) is strictly controlled in the order of injections, ointments, tablets and capsules so as to prevent cross-contamination.

In addition, according to the criteria for facilities described in the attached Table 4 of the Medical Act, it is required that an operating room have an air-conditioning system with a HEPA filter built therein in order to prevent polluted outside air from being introduced into the operating room and eliminate fine dust from indoor air. For example, it is required that the operating room involved in a transplant operation, a cochlear implantation, etc., with a low risk of infection and the operating room involved in abdominal section and laparoscopic surgery with a moderate risk of infection be ventilated at least 15 times per hour, out of which at least three times outside air needs to be introduced therein without fail. It is also required that the operating room involved in a cerebrovascular surgery, a cardiovascular surgery, etc., with a high risk of infection be ventilated at least 20 times, out of which at least three times outside air needs to be introduced therein without fail, so as to clearly maintain an inside of the operating room and control an indoor pressure within the range of 2.5 Pa to 8 Pa, thereby managing a positive pressure. It is further required that a negative pressure hospital room, which gives a medical treatment while placing patients with contagious disease such as MERS, SARS, anthrax, Ebola, etc., including those infected with or suspicious of the same under quarantine, be ventilated at least a predetermined number of times within the range of 4 to 12 times and an indoor pressure be maintained at 22.5 Pa or less. Bacteria and viruses, which are generated and suspended in a negative pressure hospital room, are spread with air as a medium. Thus, the inside of the hospital room needs to be sealed and isolated from an external environment while maintaining a lower pressure state (negative pressure) than an adjacent place. In addition, it is also required to maintain a positive pressure or a negative pressure, or a positive pressure and a negative pressure at the same time according to purposes of use, in the case of broadcasting relay vehicles, medical examination vehicles and emergency patient transport vehicles, educational promotion vehicles, chemical analysis vehicles, chemical, biological, and radiological (CBR) analysis vehicles, military communication vehicles, animal carcass collection and biological analysis vehicles, etc. which have an access to the areas described above. It is required that a driver's cabin have a separate positive pressure facility installed therein.

In addition, in the case of nuclear power generation facilities and research facilities, the emergency operating facilities (EOF) are located outside the radiation emergency planning zone (EPZ) in preparation for nuclear accidents. However, if the EOF is located inside the EPZ, it is required that a ventilation system having outside air pass through a HEPA filter (no activated carbon required) be built therein (EOF) in terms of habitability, so that researchers can be prevented from any health risk involved in radiation exposure caused by nuclear accidents, and it is also required that indoor air be recirculated by passing through the HEPA/activated carbon filter, considering a case in which the indoor air is polluted, or a duct be installed to form a uniform pressure distribution in a space where a positive pressure is required. And it is further required that positive pressure maintenance facilities be configured to receive a supply of emergency power from an emergency generator upon power outage.

In addition, it is required that an indoor pressure be at least 250 Pa in a toxic-free area (TFA) of government dispersal facilities, government buildings, and CBR facilities of military facilities, at least 210 Pa in an air lock room (AL), at least 170 Pa in a liquid hazardous area (LHA), and at least 125 Pa in an equipment store area (ESA). It is required that a ventilation volume be maintained at least 25 CMH per person in normal times, and at least 17 CMH per person in case of CBR warfare.

Considering the related art for maintaining a positive pressure of a space in which the positive pressure is to be maintained as described above, 1) Korean Patent Publication No. 10-1101356 discloses a case cover of power receiving and distribution equipment and a power receiving and distribution facility system, in which a power receiving and distribution equipment carries out a transformation by receiving power inside a case, which has a lower portion thereof opened, has a control panel formed in a front surface thereof, and has an upper portion and both sides thereof sealed, in which the power receiving and distribution equipment is installed while securing a certain space apart from the case, and supplies compressed air having a pressure higher than an atmospheric pressure into the case so as to maintain the inside of the case at a positive pressure, and save air to maintain the positive pressure when a distribution board is completely flooded, so that it is possible to control the positive pressure of the power receiving and distribution equipment, which is a unit electric equipment. However, there is a restriction on application to an enlarged space such as a substation room, a control room and an operating room, where people are working.

2) U.S. Unexamined Patent Publication No. 10-2014-0069306 and International Application No. PCT/US2012/057476 disclose an environmental control of patient room driven by admission, in which a patient's room of medical facilities (e.g., hospitals, nursing homes, and outpatient facilities) is generally designed and configured to maintain a balance among medical care, patient's comfort, and efficient operation. In the guidelines such as ASHIRAE Advanced Engineering Guide for Small Hospitals and Healthcare Facilities; LEED 2009 for Healthcare EQ Credit 6.1, Controllability of Systems: Lighting and EQ Credit 6.2, Controllability of Systems: Thermal Comfort; and FGI 2006, 2.1-10.3.5.2, it is stipulated that these facilities provide patients with an environment as best as possible while maximizing the ability to provide medical protection and operate in an efficient manner.

These guidelines provide and recommend different environmental controls for different hospital rooms. For example, a protective environment room is set to be ventilated 12 times per hour at positive pressure, and a waiting room is set to be ventilated 10 times per hour.

In order to comply with the above guidelines, a ventilation system of hospital rooms has the Heating Ventilation, Air Condition (HVAC) System built therein in advance, and has the number of ventilation adjusted according to the presence or absence of occupants or patients detected by using a real-time positioning system. Thus, the ventilation system may control ventilation, temperature, lighting, positive pressure management, etc., but the guidelines do not provide any specific matters on how to create and maintain a positive pressure atmosphere in a hospital room, and any function for sterilization of floating bacteria and viruses in the ventilated air.

3) According to Article 230 (Setup and Management of Explosion Hazardous Areas) and Articles 311 (Selection, etc. of Electrical Machines and Instruments Used in Explosion Hazardous Areas) of the Rules on Occupational Safety and Health Standards of the Occupational Safety and Health Act and the related technical guideline KOSHA GUIDE E-48-2012 (Technical Guidelines for Design, Selection, and Installation of Electrical Equipment in Gas Explosion Hazardous Places), the areas, which have an explosive atmosphere or are likely to do so due to gases that require special attentions when installing and using electrical machines and instruments, are designated as an explosion hazardous area, and then classified into "Class 0", "Class 1", and "Class 2" based on the frequency and period of the explosive atmosphere. Accordingly, it is stipulated that the electro-mechanical appliances installed in the explosion hazardous place include a suitable explosion-proof structure out of an explosion-proof structure for internal pressure (d, flameproof enclosure), an increased safety explosion-proof structure (e, increased safety), an intrinsic safety explosion-proof structure (i, intrinsic safety), and a pressurization explosion-proof structure (p, pressurization), so as to prevent any fire and explosion caused by combustible gas.

In addition, according to Article 230 (Setup and Management of Explosion Hazardous Areas) and Article 311 (Selection, etc. of Electrical Machines and Instruments Used in Dust Explosion Hazardous Areas) of the Rules on Occupational Safety and Health Standards and the related technical guideline KOSHA GUIDE E-117-2014 (Technical Guidelines for Selection and Installation of Electrical Equipment in Dust Explosion Hazardous Areas), the areas, which have a cloud-shaped combustible dust that requires special attentions when installing and using electrical machines and appliances, or need preventive measures against ignition of explosive mixtures of dust/air, are classified into "Class 20", "Class 21", and "Class 22," considering a condition under which a cloud shape of combustible dust in air continuously occurs for a long period of time, a condition under which the cloud dust frequently occurs in normal operation, or a condition under which almost on cloud dust occurs in normal operation, so that the electrical machines and appliances installed in the dust explosion hazardous areas classified as above are installed to include a suitable explosion-proof structure out of "dust explosion-proof structure for internal pressure (tD)," "dust mold explosion-proof structure (mD)," "dust intrinsic safety explosion-proof structure (iD)," and "dust pressure explosion-proof structure (pD)," so as to prevent any fires and explosions caused by combustible dust.

Moreover, according to Article 335 (Location, etc., of Substation Room) and the technical guidelines for maintaining a positive pressure in substation rooms, etc., (Kosha Guide E-98-2011), it is required to build a positive pressure system in a target space by selecting either a method of Pressurization With Leakage Compensation, in which a ventilation system is configured with air supply/discharge fans and ducts in a target space such as a substation room, a control room, etc., and has the fan activated to suction unpolluted outside air (protective gas) and supply the resulting air into the target space, so as to maintain an indoor pressure of the target space at a positive pressure higher than an atmospheric pressure (Pressurization System), so that external gas, etc., is suppressed from being introduced indoors, so as to sufficiently inject the protective gas (air) considering a predictable leakage while closing all the openings of the substation room, etc., thereby maintaining the positive pressure, or a method of Pressurization With Continuous Circulation of Protective Gas, which continuously circulates the protective gas (air) inside the substation room, etc., to maintain the positive pressure. It is also required to maintain a pressure of the target space at 25 pa (0.25 mbar) and an air velocity at 0.305 m/S or more on an open surface while all the openable openings are opened, but there is no description about technique for purifying the polluted air and sterilizing bacteria and viruses.

4) Among the radiation emergency response facilities installed and operated in preparation for nuclear accidents at nuclear power generation facilities and research facilities, it is required that the emergency operating facilities (EOF) are installed outside the radiation emergency planning zone (EPZ) in principle.

According to the Regulations on Radiation Emergency Countermeasures for Nuclear Business Operators: Nuclear Safety And Security Commission Notification No. 2014-82, Safety and "Functional Criteria for Emergency Response Facilities: NURGE-0696, U, S, NRC (1981) of Atomic Energy Commission (2014), and "Clinton Power Station Emergency Plan Implementing Procedures" of Clinton Nuclear Power Plant, there is a description about the U.S. emergency response facility requirements for the Emergency Operating Facilities (EOF) outside the Radiation Emergency Planning Zone (EPZ) in NUREG-0696. In order to prevent any health risk to researchers, etc., in relation to radiation exposure caused by nuclear accidents, it is required to build a ventilation system in which outside air passes through a HEPA filter (activated carbon) in terms of habitability and indoor air is recirculated via the HEPA/activated carbon filter considering the case in which indoor air is polluted, if the Emergency Operating Facilities (EOF) is located inside the Radiation Emergency Planning Zone (EPZ). In addition to the above requirements, the "Clinton Power Station Emergency Plan Implementing Procedures" also requires that ducts be configured to form a uniform pressure distribution in the space where a positive pressure needs to be maintained, and the positive pressure maintenance facilities be configured to receive emergency power from an emergency power generator in case of power outage. However, there is no specific solution for the removal of radioactive materials.

Considering the related art for maintaining a negative pressure in a space in which the negative pressure is to be maintained as described above, 1) Korean Patent Publication No. 10-1649600 discloses a movable system for negative pressure isolation room, which includes a negative pressure room of which the inside is sealed and isolated from an external environment to maintain a low pressure state, and a front room which is located at an outer side of an entrance to the negative pressure isolation room to maintain an indoor pressure at a relatively high pressure, so that indoor air can be blocked from being discharged outside due to a relative air pressure difference between the negative pressure room and the front room, thereby creating an isolated room where patients can be given a medical treatment. This technique maintains the negative pressure due to the relative atmospheric difference, but has no sterilization function for bacteria and floating viruses in air.

In other words, the positive pressure maintenance methods based on the Pressurization With Leakage Compensation and Pressurization With Continuous Circulation of Protective Gas, which are applied to substation rooms and control rooms, comply with requirements for positive pressure by maintaining a pressure of a target space at 25 pa (0.25 mbar) and an air velocity at 0.305 m/S or more on an open surface while all the openable openings are opened. In case of a negative pressure hospital room, which gives a medical treatment while placing patients with contagious disease including those infected with or suspicious of the same under quarantine, the positive pressure maintenance methods maintain a negative pressure due to a relative atmospheric difference between a medical room and a front room, but do not provide any criteria for purifying protective gas (air) for maintaining a positive pressure and a negative pressure and sterilizing bacteria and floating viruses. In addition, a positive pressure maintenance unit applied to pharmaceutical sectors, food sectors, medical facilities and a positive pressure chamber of a clean room type in dust-causing sectors, as well as a positive pressure facility of Emergency Operating Facilities (EOF) of nuclear power facilities have neither a function for sterilizing bacteria and viruses in introduced air and circulated air, nor a function for removing radioactive materials. Moreover, in case of special-purpose vehicles such as a chemical analysis vehicle, a chemical, biological, and radiological (CBR) analysis vehicle, etc., there is neither the function for sterilizing bacteria and viruses, nor the function for removing radioactive materials. Furthermore, there is no alarming function against an abnormal operation departing from criteria for positive and negative pressures, and thus it is impossible for managers to take an immediate action, and it is insufficient to prevent any infection of bacteria and viruses spreading with air as a medium.

DISCLOSURE

Technical Problem

A technical object of the present invention is to provide a positive pressure and negative pressure maintenance system having a bacteria sterilizing function and a harmful material and radioactive material removing function, which includes a preprocessing unit having at least one selected from first, second and third preprocessing members, an air supply member, a postprocessing unit and a control panel, and which is configured to adsorb and remove hydrogen fluoride (HF), acid gas materials, VOCs materials, etc., from introduced air by using an absorbing agent and an electrochemical reaction in a process of high-voltage discharge, have a radioactive material removing portion installed therein, thereby removing radioactive materials such as radon, cesium, etc., by an electro-adsorptive method, purify polluted air through an electrochemical reaction of high-voltage discharge in a high-voltage discharge portion, supply air generated by sterilizing floating bacteria in air into a space in which a positive pressure and a negative pressure is to be maintained by using an air supply fan, adjust a number of rotations of an air supply fan, a circulation fan and a discharge fan and adjust an opening rate of an air volume control damper according to data transmitted in real time from a detection sensor, which detects an indoor pressure of the space in which the positive pressure and the negative pressure are to be maintained, thereby maintaining an indoor pressure of the space in which the positive pressure is to be maintained at a positive pressure, dissociate harmful chemicals from polluted air containing the harmful chemicals, bacteria and viruses of the negative pressure chamber by the postprocessing unit including a high-voltage discharge member, an adsorption member and a discharge fan through an electrochemical reaction in a process of high-voltage discharge, thereby adsorbing and removing the harmful chemicals with an adsorbing agent, and sterilize the resulting air with free radicals such as superoxide anion ($O_2-$), hydroxyl radical (OH-radical), nitrogen monoxide (NO), singlet oxygen ($^1O^2$), etc., in which an oxygen ion (O) generated by dissociating a covalent bond of constituent molecule materials of air in a process of high-voltage discharge is bonded with oxygen in an unstable form so as to discharge the sterilized air into the atmosphere, thereby blocking a path of bacteria and viruses spreading with air as a medium.

Technical Solution

To solve the technical object as described above, there may be provided a positive pressure and negative pressure maintenance system having a bacteria sterilizing function and a harmful material and radioactive material removing function, which is installed inside a building including a special-purpose vehicle, and comprises: a preprocessing unit configured to select and use at least one of a first preprocessing member installed in one branch pipe of three branch pipes connected to a main pipe so as to purify polluted air, a second preprocessing member installed in another branch pipe so as to sterilize bacteria and variant viruses in air, and a third preprocessing member installed in still another branch pipe so as to remove radioactive materials; an air supply member installed at a distance from the preprocessing unit so as to supply air into a positive pressure chamber and a negative pressure chamber; a postprocessing unit installed at one side of an upper part of or one side of an upper part of a side surface of the negative pressure chamber so as to sterilize bacteria and floating viruses in polluted air and discharge a resulting air to an outside; and a control panel configured to perform a control by supplying power to or cutting off power from the preprocessing unit, the air supply member, and the postprocessing unit by a control program, which is programmed and inputted in advance according to data on a pressure and a concentration of harmful materials measured in real time by a detection sensor installed in a space in which a positive pressure and a negative pressure are to be maintained.

The first preprocessing member may include a high-voltage discharge member and an adsorption member inside a housing, so that the polluted air containing harmful materials may be ionized with a covalent bond of a harmful material molecule dissociated in a process of high-voltage discharge and may be then adsorbed onto an adsorption material loaded on a carrier of an adsorption member so as to purify the polluted air.

The second preprocessing member may include a first high-voltage discharge member, an adsorption member and a second high-voltage discharge member inside a housing, so that the polluted air containing harmful materials may be ionized with a covalent bond of a harmful material molecule dissociated in a process of high-voltage discharge and may be then adsorbed onto an adsorption material loaded on a carrier of the adsorption member so as to purify the polluted air, and then to sterilize bacteria and variant viruses in air, which are introduced, with free radicals such as superoxide anion ($O_2-$), hydroxyl radical (OH-radical), nitrogen monoxide (NO), singlet oxygen ($^1O_2$), etc., in which an oxygen ion (O) generated by dissociating a covalent bond of nitrogen ($N_2$), oxygen ($O_2$) and a water molecule ($H_2O$) of water vapor, which are constituent materials of purified air, may be bonded with oxygen in an unstable form.

The third preprocessing member may include a high-voltage discharge member, a hydrogen gas generator, and an electric adsorption portion and is so configured that the polluted air containing radioactive materials may be ionized by dissociating a covalent bond of a harmful material molecule in a process of high-voltage discharge, a hydrogen gas generated from a hydrogen generator may be injected into a resulting ionized air and mixed together, and an air containing radioactive materials mixed with hydrogen may have the radioactive materials adsorbed onto an ion exchange resin layer coated onto an outer surface of a discharge electrode and a ground electrode of the electric adsorption portion, while high voltage may be applied to the discharge electrode and the ground electrode at the same time, so that the radioactive materials on the ion exchange resin layer may be activated and adsorbed onto the resin layer with a hydrogen molecule dissociated into a hydrogen cation, thereby removing the radioactive materials through a reduction reaction of the radioactive materials in association with the hydrogen cation and an activated metal ion of the ion exchange resin layer.

The air supply member may include an air supply fan, in which at least one fan selected from sirocco, airfoil, turbo and blower type fans may be installed to pressurize outside air, and an air volume control damper which is installed in the branch pipe connected to the main pipe and branched off from the main pipe and connected with the positive pressure chamber so as to supply the air supplied by the air supply fan into the positive pressure chamber, and which may be also installed in the branch pipe branched off from the main pipe and connected to the negative pressure chamber.

The postprocessing unit may have a fan and a high-voltage discharge member installed inside an independent housing, so as to suction and pressurize a polluted indoor air of a space in which a negative pressure is to be maintained and supply a resulting air into the high-voltage discharge member by using the fan, thereby sterilizing bacteria and floating viruses in the polluted air with free radicals such as superoxide anion ($O_2-$), hydroxyl radical (OH-radical), nitrogen monoxide (NO), singlet oxygen ($^1O_2$), etc., in which an oxygen ion (O) generated in a process of high-voltage discharge may be bonded with oxygen in an unstable form.

The high-voltage discharge member of the first preprocessing member of the preprocessing unit may include a discharge electrode, a ground electrode, a high-voltage generator, and a conducting wire, in which the adsorption member may include a grid, a cage, a DC power supply, a conducting wire and an adsorption material loaded on a carrier, so as to primarily remove harmful materials from the air containing the harmful materials, which is introduced to the high-voltage discharge member, through an electrochemical reaction such as dissociation, ionization, excitation, oxidation, reduction reaction, etc. in a process of high-voltage discharge and then adsorb and remove surplus harmful materials in a primarily purified air with the adsorption material loaded on the carrier of the adsorption member.

The adsorption member may have the carrier and the adsorption material installed therein, in which the carrier for adsorbing acid gas such as hydrogen chloride (Hcl), chlorine ($Cl_2$), sulfur dioxide ($SO_2$), hydrogen sulfide ($H_2S$), etc., may be activated carbon, in which an adsorbing agent loaded on the carrier may include at least one selected from iron sulfate, ammonium iron sulfate, iron oxide, iron nitrate, iron hydroxide, and iron chloride, and at least one selected from zinc sulfate, ammonium zinc sulfate, zinc oxide, zinc hydroxide, zinc nitrate, and zinc chloride, so that the adsorption material where the ion compound and the zinc chloride material are mixed may be loaded on an activated carbon carrier, in which the carrier for adsorbing hydrogen fluoride (HF) gas may include at least one material selected from porous polymers such as styrene-based polymer, acryl-based polymer, methacryl-based polymer, vinyl-based polymer, and urethane-based polymer, in which the adsorption material may include at least one material selected from ethylamine, butylamine, hexylamine, octylamine, decylamine, dodecylamine, tetradecylamine, hexadecylamine, octadecylamine, ethylenediamine, tetramethylenediamine, and hexamethylenediamine and may be loaded on the porous carrier, and in which an adsorption material of formaldehyde, acetaldehyde, toluene, xylene, paradichlorobenzene, ethylbenzene, styrene, chlorpyrifos, di-n-butyl phthalate, di-2-ethylhexyl tetradecane phthalate, diazinone, fenobucarb, and volatile organic compound (VOCs) materials, may include at least one material selected from globular zeolite (ZSM-5, ZSM-8), activated alumina or pellet-type activated carbon and may be filled into a case without a separate carrier.

The second preprocessing member may include the first high-voltage discharge member, the adsorption member and the second high-voltage discharge member, in which the first high-voltage discharge member may include a discharge electrode, a ground electrode, a high-voltage generator, and a conducting wire, in which the adsorption member may include a grid, a cage, a DC power supply, a conducting wire and an adsorption material loaded on a carrier, and in which the second high-voltage discharge member may include a discharge electrode, a ground electrode and a high-voltage generator for supplying high voltage to the electrodes through a conducting wire, so as to primarily purify an air containing contaminants, which is introduced to the first high-voltage discharge member, through an electrochemical reaction such as dissociation, ionization, excitation, oxidation, reduction reaction, etc. in a process of high-voltage discharge, adsorb and remove surplus contaminants in a primarily purified air with the adsorption material loaded on the carrier of the adsorption member, and sterilize bacteria and floating viruses in air, which is introduced, with free radicals such as superoxide anion ($O_2$—), hydroxyl radical (OH-radical), nitrogen monoxide (NO), singlet oxygen ($^1O_2$), etc., in which an oxygen ion (O) generated by dissociating a covalent bond of nitrogen ($N_2$), oxygen ($O_2$) and a water molecule ($H_2O$) of water vapor, which are constituent materials of air purified by the second high-voltage discharge member, may be bonded with oxygen in an unstable form.

The adsorption member of the first preprocessing member may include a grid, a cage, a DC power supply, a conducting wire, and an adsorption material loaded on a carrier, and the adsorption member of the second preprocessing member may include a grid, a cage, a DC power supply, a conducting wire and an adsorption material loaded on a carrier, in which a negative pole of the DC power supply may be connected to the grid and a positive pole of the DC power supply is connected to the cage, so that attractive force may work between the cage and the carrier filled inside the cage, thereby enhancing an adsorption rate of harmful materials.

The third preprocessing member may include the high-voltage discharge member including the discharge electrode, the ground electrode and a high-voltage generator configured to supply high voltage to the electrodes through a conducting wire, the hydrogen gas generator including a housing, a tap water supply pipe, an electrolyte supply portion, an alkali metal power supply portion, a first solenoid coil, a second solenoid coil, a fan, an electromagnetic valve, a heating coil and an injection nozzle, or including a hydrogen gas bombe, a pressure reducer, a flow control valve and a supply pipe, and the electric adsorption portion including a dehumidifying filter having a housing and a dehumidifying agent, the ion exchange resin layer, the discharge electrode and the ground electrode having the ion exchange resin layer coated on an outer surface thereof, and a high-voltage generator.

The electrolyte supply portion may include a storage container, a supply pipe and an electromagnetic valve, in which an electrolyte stored in the storage container may include at least one material selected from the group consisting of potassium chloride, sodium chloride, calcium chloride, lithium chloride, potassium nitrate, sodium nitrate, potassium sulfate and a mixture thereof, and may be stored in the storage container and then used.

The alkali metal powder supply portion may include a storage container, a supply pipe, and an electromagnetic valve, in which at least one material selected from magnesium, lithium, sodium, and potassium may be stored in the storage container and then used.

The first solenoid coil may have a coil with a predetermined diameter wound around one side portion of an outer surface of the housing, and may have a coil with a predetermined diameter wound by a predetermined number of turns around one side of an outside of a rod having a predetermined diameter and a predetermined length, which may be installed in an inner center of the housing, and the second solenoid coil may be installed at a distance apart from an inner surface of the housing and the first solenoid coil installed in a center of the housing, in which winding directions of the first solenoid coil and the second solenoid coil may be opposite to each other, in which a mixed solution of tap water, electrolyte and alkali metal power inside the housing flows by a magnetic field and Lorentz's force respectively in a direction perpendicular to a direction of electric current flow of the first and second solenoid coils so as to increase an amount of hydrogen generated, and in which power may be supplied to the first and second solenoid coils having coils wound in directions opposite to each other, so that magnetic fields generated in a direction vertical to a direction of electric current flow may be generated in directions opposite to each other, and thus zero-field (SE) energy generated by superimposed magnetic fields may more activate the mixed solution of tap water, electrolyte and alkali metal powder, thereby increasing an amount of hydrogen generated.

The radioactive materials and the hydrogen gas may be introduced into the third preprocessing member by a suction force of the air supply fan of the air supply member, so that the radioactive materials may be adsorbed onto the ion exchange resin layer coated on an outer surface of the discharge electrode and the ground electrode and may be subject to a first oxidation reaction with a functional group contained in resin, and the hydrogen gas may be dissociated into a hydrogen atom (H) between the discharge electrode and the ground electrode so as to remove the reactive materials such as lead isotope ($^{210}Pb$), cesium (CS), uranium isotope ($^{234}$, $^{238}U$), thorium isotope ($^{230}Th$), radium isotope ($^{220}Ra$), radon isotope ($^{222}Rn$), polonium isotope ($^{210}$, $^{218}Po$), lead (Pb) isotope ($^{210}Pb$), etc. through a reduction reaction.

An indoor pressure control of the positive pressure chamber and the negative pressure chamber may be performed by at least one method selected from a method, in which an indoor pressure may be detected by each detection sensor installed indoors and transmitted to a control panel, so as to adjust a number of rotations (RPM) of the fan, which may supply, circulate and discharge air into the positive pressure chamber and the negative pressure chamber, according to a control circuit, which may be programmed and inputted in advance, thereby adjusting an air volume to be supplied and discharged into the positive pressure chamber and the negative pressure chamber, or a method in which an opening rate of the air volume control damper installed in an air supply, discharge and circulation pipeline may be adjusted or an operator checks an indicated value of a differential pressure gauge installed in the positive pressure chamber and the negative pressure chamber, so as to adjust an opening rate of the damper installed in the air supply, discharge and circulation pipeline, so that the control panel may sound an alarm when an indoor pressure is less than or more than a set value and automatically adjust the number of rotations (RPM) of fans and an opening rate of the air volume control damper, thereby maintaining the indoor pressure within a set range.

Advantageous Effects

A positive pressure and negative pressure maintenance system having a bacteria sterilizing function and a harmful material and radioactive material removing function according to the present invention has an advantage of removing harmful chemicals and radioactive materials from the air to supplied into a positive pressure chamber and a negative pressure chamber, thereby preventing a health impairment factor for occupants.

In addition, the present invention has an advantage of purifying contaminants, which are discharged from the negative pressure chamber to the outside, and sterilizing bacteria and floating viruses to be discharged, so as to block a path of contagious bacterial infection with air as a medium, thereby preventing harmfulness in terms of public health.

Furthermore, the present invention has an advantage of adjusting a rotating speed (RPM) of air supply and discharge fans by a control circuit of a control panel according to data which are measured and transmitted in real time by a pressure sensor installed in a space in which a positive pressure and a negative pressure are to be maintained, and adjusting an opening rate of an electromotive damper so as to efficiently maintain a positive pressure and a negative pressure of the space in which the positive and negative pressures are to be maintained.

Besides, the present invention has an advantage of applying the positive pressure and negative pressure maintenance system of the present invention to a special-purpose vehicle, thereby securing safety for researchers from a hazardous risk of an accident site.

BEST MODE

Hereinafter, a preferred embodiment of a positive pressure and negative pressure maintenance system having a bacteria sterilizing function and a harmful material and radioactive material removing function according to the present invention will be described in detail with reference to the accompanying drawings.

First, the positive pressure and negative pressure maintenance system having a bacteria sterilizing function and a harmful material and radioactive material removing function according to a preferred embodiment of the present invention will be described with reference to FIG. 1.

Figure 1:
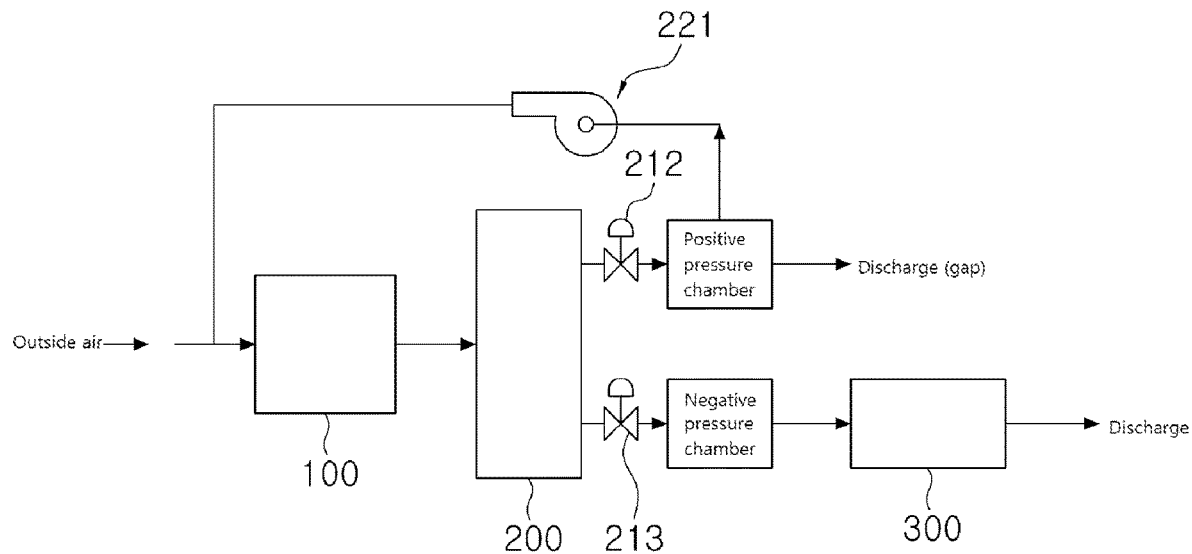
FIG. 1 is a view showing a configuration for explaining a positive pressure and negative pressure maintenance system having a bacteria sterilizing function and a harmful material and radioactive material removing function according to a preferred embodiment of the present invention.

FIG. 1 is a view showing a configuration for explaining a positive pressure and negative pressure maintenance system having a bacteria sterilizing function and a harmful material and radioactive material removing function according to a preferred embodiment of the present invention.

Referring to FIG. 1, the positive pressure and negative pressure maintenance system having a bacteria sterilizing function and a harmful material and radioactive material removing function according to a preferred embodiment of the present invention (hereinafter, "positive pressure and negative pressure maintenance system") may include a preprocessing unit 100, an air supply member 200, a postprocessing unit 300 and a control panel 400.

The preprocessing unit 100 may include a first preprocessing member 110 installed in one of three branch pipes connected to a main pipe, a second preprocessing member 120 installed in another branch pipe, and a third preprocessing member 130 installed in still another branch pipe.

The first preprocessing member 110 may have a high-voltage discharge member 111 and an adsorption member 112 installed inside a housing 101, in which outside air may be introduced into the high-voltage discharge member 111 by a suction force of an air supply fan 211 of the air supply member 200 and may be subject to an electrochemical reaction such as dissociation, excitation, ionization, oxidation, reduction, etc. so as to decompose a covalent bond of contaminants such as ammonia ($NH_3$), formaldehyde (HCHO), hydrogen fluoride (HF), etc., contained in air, resulting in dissociation into ions such as a hydrogen cation (H+), aldehyde (CHO—), fluorine ion (F+), etc., thereby adsorbing and removing harmful materials with an adsorption material 112*f* loaded on a porous carrier 112*e*.

The second preprocessing member 120 may have a first high-voltage discharge member 122, an adsorption member 123 and a second high-voltage discharge member 124 installed inside a housing 121, in which outside air may be introduced into the first high-voltage discharge member 122 by a suction force of the air supply fan 211 of the air supply member 200 and may be subject to an electrochemical reaction such as dissociation, excitation, ionization, oxidation, reduction, etc. so as to decompose a covalent bond of contaminants such as ammonia ($NH_3$), formaldehyde (HCHO), hydrogen fluoride (HF), etc., contained in air, resulting in dissociation into ions such as a hydrogen cation (H+), aldehyde (CHO—), fluorine ion (F+), etc., thereby adsorbing and removing harmful materials with an adsorption material 123*f* loaded on a porous carrier 123*e*, and attacking a cellular wall of bacteria such as fungi, *Pseudomonas aeruginosa, Staphylococcus aureus*, pneumococcus, *Legionella*, etc., and floating viruses such as variant virus (MRSA), MERS coronavirus (MERS-COV), Ebola virus, Sascorona virus (SARS-COV), bacteria, etc., in the introduced air, with free radicals such as superoxide anion ($O_2$—), hydroxyl radical (OH-radical), nitrogen monoxide (NO), singlet oxygen ($^1O_2$), etc., including an active radical such as hydroxyl radical (OH-radical), in which an oxygen ion (O) generated in a process of second high-voltage discharge may be bonded with oxygen in an unstable form, resulting in decomposition and perforation of the cellular wall, damage to biological tissues and organs, and sterilization.

The third preprocessing member 130 may include a high-voltage discharge member 131, a hydrogen gas generator 132, a dehumidifying filter 134, and an electric adsorption portion 135, in which outside air may be introduced into the high-voltage discharge member 131 by a suction force of an air supply fan 211 of the air supply member 200 and may be subject to an electrochemical reaction such as dissociation, excitation, ionization, oxidation, reduction, etc. so as to decompose a covalent bond of contaminants such as ammonia (NH3), formaldehyde (HCHO), hydrogen fluoride (HF), etc., contained in air, resulting in dissociation into ions such as a hydrogen cation (H+), aldehyde (CHO−), fluorine ion (F+), etc., after which the hydrogen gas produced from the hydrogen gas generator 132 may be injected into the dissociated outside air through a nozzle installed in a pipeline and mixed together, then introduced into a dehumidifying filter 134 to dehumidify a part of moisture in air, and then transferred to the electric adsorption portion 135, so that DC power may be supplied to a discharge electrode 135c and a ground electrode 135d having ion exchange resin layers 135a and 135b coated on an outer surface of the electric adsorption portion 135 so as to start discharge between the discharge electrode 135c and the ground electrode 135d and activate metal ions of the ion exchange resin layers 135a and 135b, thereby carrying out an oxidation reaction with ionic materials in the introduced outside air, while removing radioactive materials through a reduction reaction with a hydrogen cation (H+) produced by decomposing a hydrogen molecule during discharge.

The air supply member 200 may include an air supply fan 211, in which at least one fan selected from sirocco, airfoil, turbo and blower type fans may be installed at a distance apart from the preprocessing member 100 so as to pressurize outside air, and may be so configured that an air volume control damper 212 may be installed in a main pipe 214 connected to and branched off from a main pipe and connected with the positive pressure chamber so as to supply the air supplied by the air supply 211 fan into the positive pressure chamber, a circulation fan 221 may be installed in a circulation pipe to circulate a part of air of the positive pressure chamber into the preprocessing unit, and an air volume control damper 213 may be installed in a branch pipe 215 branched off from the main pipe 214 and connected to the negative pressure chamber so as to supply air into the negative pressure chamber.

The postprocessing unit 300 may be installed at one side of an upper part of or one side of an upper part of a side surface of a negative pressure maintenance space, and may have a discharge fan 311 and a first high-voltage discharge member 312 installed inside an independent housing 301, so as to suction and pressurize a polluted indoor air in the negative pressure maintenance space and supply the resulting air into the high-voltage discharge member 312 by using the discharge fan 311, thereby attacking a cellular wall of bacteria such as fungi, Pseudomonas aeruginosa, Staphylococcus aureus, pneumococcus, Legionella, etc., and floating viruses such as variant virus (MRSA), MERS coronavirus (MERS-COV), Ebola virus, Sascorona virus (SARS-COV), bacteria, etc., in the introduced air, with free radicals such as superoxide anion ($O_2$—), hydroxyl radical (OH-radical), nitrogen monoxide (NO), singlet oxygen ($^1O_2$), etc., including an active radical such as hydroxyl radical (OH-radical), in which an oxygen ion (O) generated by dissociating a covalent bond of air constituent molecules in a process of high-voltage discharge may be bonded with oxygen in an unstable form, resulting in decomposition and perforation of the cellular wall, damage to biological tissues and organs, and sterilization.

The control panel 400 may perform a control by supplying power to or cutting off power from the preprocessing unit 100, the air supply member 200, and the postprocessing unit 300 by a control program, which is programmed and inputted in advance according to data on a pressure and a concentration of harmful materials measured in real time by detection sensors 411 and 412 installed in a space in which the positive pressure and the negative pressure are to be maintained.

Figure 2:
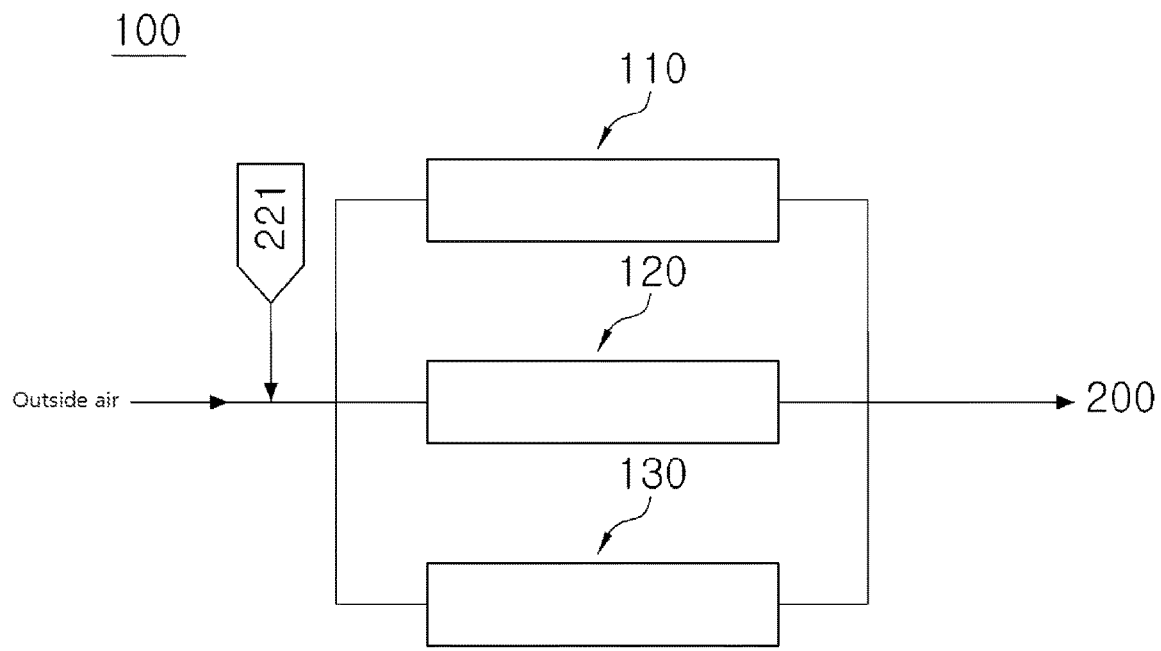
FIG. 2 is a view showing a detailed configuration of a preprocessing unit illustrated in FIG. 1.

FIG. 2 is a view showing a detailed configuration of a preprocessing unit illustrated in FIG. 1.

Referring to FIG. 2, the preprocessing unit 100 may include a first preprocessing member 110, a second preprocessing member 120 and a third preprocessing member 130, which are connected to a plurality of branch pipes branched off from a main pipe, into which polluted air is introduced, respectively.

The first preprocessing member 110 may include a high-voltage discharge member 111 and an adsorption member 112. The second preprocessing member 120 may include a first high-voltage discharge member 122, an adsorption member 123, and a second high-voltage discharge member 124. The third preprocessing member 130 may include a high-voltage discharge member 131, a hydrogen gas generator 132, a dehumidifying filter 134, and an electric adsorption portion 135 having ion exchange resin layers 135a and 135b coated on an outer surface of electrodes 135c and 135d.

In addition, at least one of the first preprocessing member 110, the second preprocessing member 120, and the third preprocessing member 130 may be selected and connected to the main pipe without a plurality of branch pipes installed in the main pipe according to the purpose of use.

Figure 3:
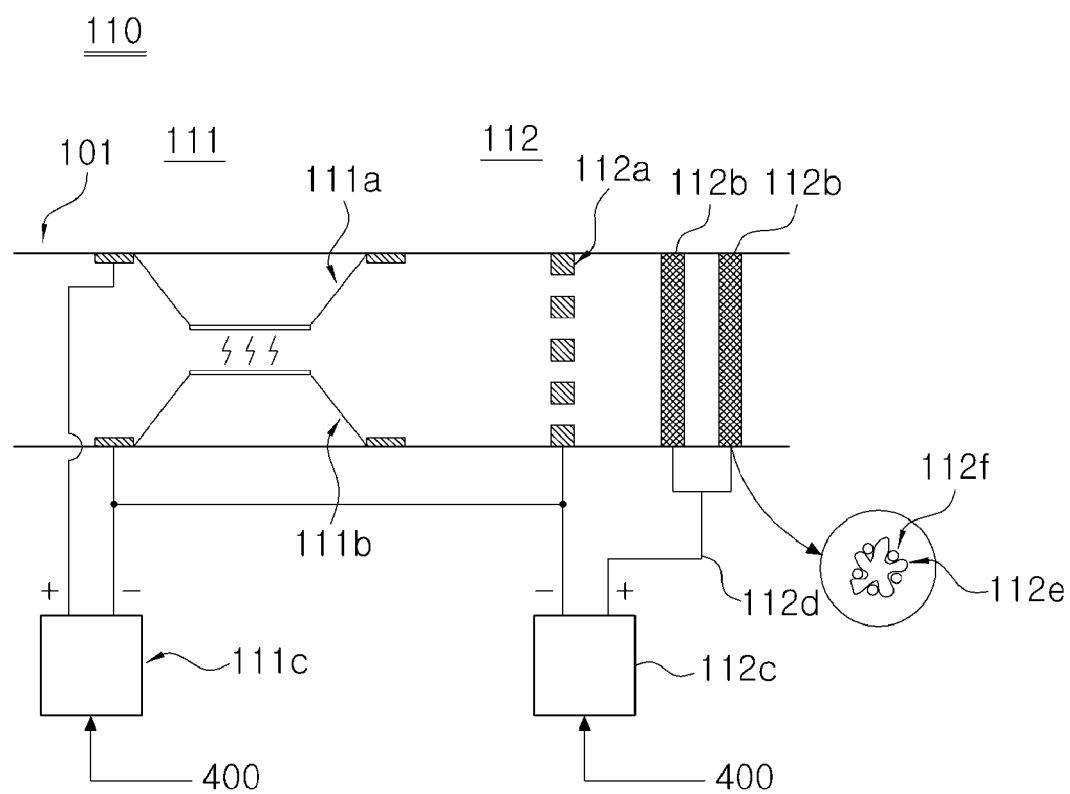
FIG. 3 is a partial sectional view showing a first preprocessing member illustrated in FIG. 2 in detail.

FIG. 3 is a partial sectional view showing a first preprocessing member illustrated in FIG. 2 in detail.

Referring to FIG. 3, the first preprocessing member 110 may include a high-voltage discharge member 111 and an adsorption member 112.

The high-voltage discharge member 111 may include a housing 101, a discharge electrode 111a and a ground electrode 111b, which are installed to face each other inside the housing, and a high-voltage generator 111c, which supplies high voltage to the electrodes 111a and 111b through a conducting wire.

The adsorption member 112 may include a grid 112a, a cage 112b, a DC power supply 112c, a conducting wire 112d, and an adsorption material 112f loaded on a carrier 112e.

The grid 112a may be made of a metal material of stainless steel in which a plurality of holes having a predetermined diameter are formed, and may be connected to a negative pole of the DC power supply 112c.

The cage 112b may be made of a metal material of stainless steel in which a plurality of holes having a predetermined diameter are formed on an outer surface thereof, and may include a cuboid shape and a porous carrier 112e, on which an adsorption material 112f of adsorbing harmful materials therein is loaded.

Accordingly, the adsorption member 112 may be applied to a preprocessing process of positive pressure equipment applied to a control panel which is installed in a place where acid gases such as chlorine may stay in a chlorine disinfection process in water treatment facilities and also a preprocessing process of positive pressure equipment installed in control rooms and evacuation shelters where biochemical gases may stay, with regard to companies, research institutes and corresponding laboratories of universities which are subject to Article 230 (Setup and Management of Explosion Hazardous Areas), Articles 311 (Selection, etc. of Electrical Machines and Instruments Used in Dust Explosion Hazardous Areas), and Article 335 (Location, etc., of Substation Rooms) of the Rules on Occupational Safety and Health Standards, as well as the related technical guideline on positive pressure maintenance in substation rooms, etc. (Kosha Guide E-98-2011). In addition, the adsorption member 112 may be applied to preprocessing equipment of positive pressure facilities for a fire-fighting decontamination vehicle, a chemical analysis vehicle, and a vehicle for sample collection and analysis in places where avian influenza (AI), foot-and-mouth disease (FMD) and coronavirus occur, which are operated by the Centers for Disease Control and Prevention.

If the high-voltage discharge member 111 receives DC power from the control panel 400 and a high voltage generated from the high-voltage generator 111c is applied to the discharge electrode 111a and the ground electrode 111b through a conducting wire, a very high field electron energy band may be created to start discharge between two electrodes 111a and 111b.

A positive pole of the high-voltage generator 111c may be connected to the discharge electrode 111a, and a negative pole of the high-voltage generator 111c may be connected to the ground electrode 111b and then connected to a grid 112a of the adsorption member 112 so as to form a bias voltage.

The polluted air containing harmful chemicals, which is introduced into the housing 101 by a suction force of the air supply fan 211 of the air supply member 200, may pass between the electrodes 111a and 111b, during which high field electron energy formed between the electrodes may be applied to the polluted air, so as to dissociate a covalent bond of harmful chemicals such as hydrogen chloride (Hcl), chlorine ($Cl_2$), hydrogen fluoride (HF), formaldehyde (HCHO), acetaldehyde ($CH_3CHO$), toluene ($C_7H_8$), xylene ($C_8H_{10}$), ethylbenzene ($C_8H_{10}$), styrene ($C_8H_8$), etc., thus resulting in ionization.

In addition, the high voltage generated by the high-voltage generator 111c may be applied to the electrodes 111a and 11b and the field electron energy generated between the electrodes 111a and 111b may be applied to primarily purify the contaminants in air through an electrochemical reaction such as dissociation, excitation, ionization, oxidation and reduction, so that the polluted air containing surplus contaminants in an ionic state may be transferred to the adsorption member 112 installed at a distance.

The adsorption member 112 may include a grid 112a, a cage 112b, a DC power supply 112c, a conducting wire 112d, and an adsorption material 112f loaded on a carrier 112e, and the grid 112a may be made of a metal material of stainless steel, in which a plurality of holes having a predetermined diameter are formed, and may be connected to a negative pole of the DC power supply 112c and connected to the ground electrode 111b of the high-voltage discharge member 111.

The cage 112b may be made of a metal material of stainless steel, in which a plurality of holes having a predetermined diameter may be formed on an outer surface thereof and may have a cuboid shape, in which conductive activated carbon, which is the carrier 112e for adsorbing acid gases such as hydrogen chloride (Hcl), chlorine ($Cl_2$), sulfur dioxide ($SO_2$), hydrogen sulfide ($H_2S$), etc., may be provided therein, and at least one selected from iron sulfate, ammonium iron sulfate, iron oxide, iron nitrate, iron hydroxide, and iron chloride, and at least one selected from zinc sulfate, ammonium zinc sulfate, zinc oxide, zinc hydroxide, zinc nitrate, and zinc chloride may be selected, so that the adsorption material 112f where the iron compound and the zinc chloride material are mixed may be loaded on an activated carbon carrier 112e.

In addition, the carrier 112e for adsorbing hydrogen fluoride (HF) gas may include at least one material selected from porous polymers such as styrene-based polymer, acryl-based polymer, methacryl-based polymer, vinyl-based polymer, and urethane-based polymer, and the adsorption material 112f may include at least one material selected from ethylamine, butylamine, hexylamine, octylamine, decylamine, dodecylamine, tetradecylamine, hexadecylamine, octadecylamine, ethylenediamine, tetramethylenediamine, and hexamethylenediamine and may be then loaded on the porous carrier (112e).

In addition, the adsorption material 112f of formaldehyde, acetaldehyde, toluene, xylene, paradichlorobenzene, ethylbenzene, styrene, chlorpyrifos, di-n-butyl phthalate, tetradecane di-2-ethylhexyl phthalate, diazinone, fenobucarb, and volatile organic compound (VOCs) materials, may include at least one material selected from zeolite (ZSM-5, ZSM-8) mixed with globular conductive activated carbon, activated alumina or pellet-type activated carbon and may be filled into a cage 123b without a separate carrier 112e. Then, if power is supplied to a DC power supply 112c through a control panel 400 while a primarily purified air is introduced in a process of high-voltage discharge of the high-voltage discharge portion, repulsive force may work in the grid and be applied to ionic materials produced in a process of discharge of the high-voltage discharge portion so as to disturb a flow of the ionic materials, thereby extending a retention time, enhancing a reaction efficiency between unreacted contaminants and ion materials, and improving contact efficiency between contaminants and ion materials while passing through a plurality of holes having a predetermined diameter in the grid. Also, attractive force may work between the case connected to a positive pole of the DC power supply 112c and the conductive activated carbon carrier 112e filled inside the case, so as to enhance adsorption efficiency of ionized contaminants.

Activated carbon, alumina, zeolite, etc. may serve as the adsorption material 112f widely used for adsorption. The materials described above may adsorb contaminants in air.

In addition, good adsorption properties may result from a highly porous or spiral surface structure that provides an increased surface area.

In particular, activated carbon may be widely used to protect people from inhalation of various toxic or harmful vapors, including toxic gases, industrial chemicals, solvents, and odorous compounds. The surface porosity of activated carbon may be typically caused by oxidation controlled during preparation. Activated carbon may be derived from, for example, coconut shell charcoal and can be prepared in the form of powders, granules and shaped products. Important features of commercial activated carbon products may include those related to pore structure and particle size. In other words, as the pore has a finer diameter and the particle size becomes smaller, a surface area may be increased to improve an adsorption performance.

Figure 4:
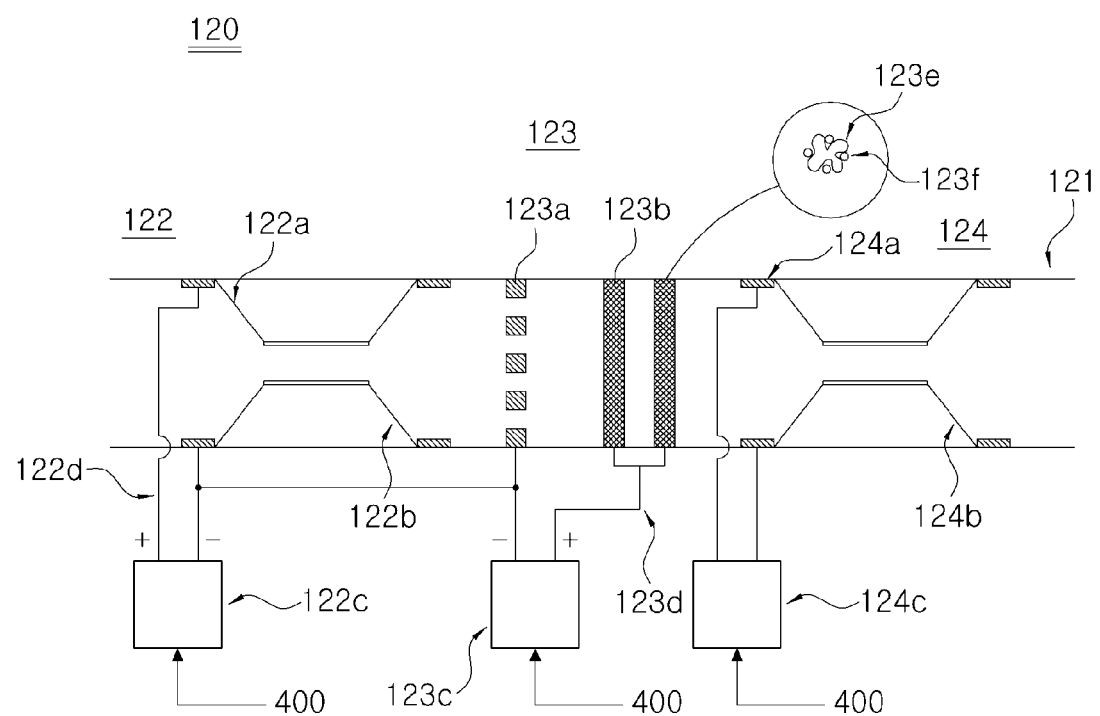
FIG. 4 is a partial sectional view showing a second preprocessing member illustrated in FIG. 2 in detail.

FIG. 4 is a partial sectional view showing a second preprocessing member illustrated in FIG. 2 in detail.

Referring to FIG. 4, the second preprocessing member 120 may include the first high-voltage discharge member 122, the adsorption member 123 and the second high-voltage discharge member 124, and may be applied to an operating room and an isolation room of medical institutions subject to the provisions of the attached Table 4 of Article 14 of the Medical Act, a genetic laboratory of companies, research institutions and related laboratories of universities subject to the Laboratory Safety Management Act, government dissipation facilities, government buildings and military facilities, likely to be exposed to biological harmfulness, livestock breeding facilities for preventing foot-and-mouth disease (FMD) and avian influenza (AI), multi-use facilities involved in potential spread of bacteria such as fungi, *Pseudomonas aeruginosa, Staphylococcus aureus*, pneumococcal, *Legionella*, etc., and floating viruses such as variant virus (MRSA), MERS coronavirus (MERS-COV), Ebola virus, Sascorona virus (SARS-COV), bacteria, etc., a preprocessing step of the positive pressure equipment such as an air dome installed in a process of destroying livestock and reprocessing buried carcasses.

The first high-voltage discharge member 122 may include a housing 121, a discharge electrode 122a and a ground electrode 122b, which are installed to face each other inside the housing 121, and a high-voltage generator 122c, which supplies DC high voltage to the electrodes 122a and 122b through a conducting wire.

The adsorption member 123 may include a grid 123a, a cage 123b, a DC power supply 123c, a conducting wire 123d, and an adsorption material 123f loaded on a carrier 123e. The grid 123a may be made of a metal material of stainless steel in which a plurality of holes having a predetermined diameter are formed, and may be connected to a negative pole of the DC power supply 123c. The cage 123b may be made of a metal material of stainless steel in which a plurality of holes having a predetermined diameter are formed on an outer surface thereof, and may include a cuboid shape and a porous carrier 123e, on which an adsorption material 122f of adsorbing harmful materials therein is loaded.

The second high-voltage discharge member 124 may include a discharge electrode 124a and a ground electrode 124b, which are installed at a distance from the adsorption member 123 to face each other inside the housing 121, and a high-voltage generator 124c, which supplies high voltage to the electrodes 124a and 124b through a conducting wire.

If the first high-voltage discharge member 122 receives DC power from the control panel 400 and a high voltage generated from the high-voltage generator 122c is applied to the discharge electrode 122a and the ground electrode 122b through a conducting wire, a very high field electron energy band may be created to start discharge between two electrodes 122a and 122b.

A positive pole of the high-voltage generator 122c may be connected to the discharge electrode 122a, and a negative pole of the high-voltage generator 122c may be connected to the ground electrode 122b and then connected to a grid 123a of the adsorption member 123 so as to form a bias voltage.

The polluted air containing harmful chemicals, which is introduced into the housing 121 by a suction force of the air supply fan 211 of the air supply member 200, may pass between the electrodes 122a and 122b, during which high field electron energy formed between the electrodes 122a and 122b may be applied to the polluted air, so as to dissociate a covalent bond of chlorohexidine gluconate, which is an antiseptic for disinfecting hand and skin and disinfecting a surgical site, isopropyl alcohol, which is a hand sanitizer, and besetine solution (volatilized vapor), which is an antiseptic for torn wound, burn, ulcer and abscess, resulting in ionization. In addition, the high voltage generated by the high-voltage generator 122c may be applied to the electrodes 122a and 122b and the field electron energy generated between the electrodes 122a and 122b may be applied to primarily purify the contaminants in air through an electrochemical reaction such as dissociation, excitation, ionization, oxidation and reduction, so that the polluted air containing surplus contaminants in an ionic state may be transferred to the adsorption member 123 installed at a distance.

The adsorption member 123 may include a grid 123a, a cage 123b, a DC power supply 123c, a conducting wire 123d, and an adsorption material 123f loaded on a carrier 123e, and the grid 123a may be made of a metal material of stainless steel, in which a plurality of holes having a predetermined diameter are formed, and may be connected to a negative pole of the DC power supply 123c and connected to the ground electrode 124b of the high-voltage discharge member 122.

The cage 123b may be made of a metal material of stainless steel in which a plurality of holes having a predetermined diameter are formed on an outer surface thereof and may include a cuboid shape. The adsorption material 123f for adsorbing chlorohexidine gluconate, isopropyl alcohol and besetine solution (volatilized vapor) may include at least one material selected from zeolite (ZSM-5, ZSM-8) mixed with globular conductive activated carbon, activated alumina mixed with conductive activated carbon, or pellet-type activated carbon and may be filled into a cage 123b without a separate carrier 112e. Then, if power is supplied to a DC power supply 123c through the control panel 400 while a primarily purified air is introduced in a process of high-voltage discharge of the high-voltage discharge portion, repulsive force may work in the grid (negative pole) 123a and be applied to ionic materials produced in a process of discharge of the high-voltage discharge portion so as to disturb a flow of the ion materials, thereby extending a retention time, enhancing a reaction efficiency between unreacted contaminants and ion materials, and improving contact efficiency between contaminants and ion materials while passing through a plurality of holes having a predetermined diameter in the grid. Also, attractive force may work between the case connected to a positive pole of the DC power supply 123c and the conductive activated carbon carrier filled inside the case, so as to attract the ionized contaminants to the carrier and the adsorbing agent by electrical attractive force, thereby enhancing adsorption efficiency.

The air purified by adsorbing harmful gases through the adsorption member 123 may be transferred into the second high-voltage discharge member 124. If the second high-voltage discharge member 124 receives AC power from the control panel 400 and a high voltage generated from the high-voltage generator 124c is applied to the discharge electrode 124a and the ground electrode 124b through a conducting wire, a very high field electron energy band may be created to start discharge between two electrodes 124a and 124b.

The air purified by adsorbing contaminants in the adsorption member 123 may be transferred, after which the high voltage generated from the high-voltage generator 124c may be applied to the electrodes 124a and 124b so as to apply field electron energy generated between the electrodes 124a and 124b, thereby attacking a cellular wall of bacteria such as fungi, *Pseudomonas aeruginosa, Staphylococcus aureus*, pneumococcus, *Legionella*, etc., and floating viruses such as variant virus (MRSA), MERS coronavirus (MERS-COV), Ebola virus, Sascorona virus (SARS-COV), bacteria, etc., in the introduced air, with free radicals such as superoxide anion (O2-), hydroxyl radical (OH-radical), nitrogen monoxide (NO), singlet oxygen (1O2), etc., including an active radical such as hydroxyl radical (OH-radical), in which an oxygen ion (O) generated by dissociating an oxygen molecule (O2), a nitrogen molecule (N2) and a water molecule (H2O) of water vapor may be bonded with oxygen in an unstable form, resulting in decomposition and perforation of the cellular wall, damage to biological tissues and organs, and sterilization of bacteria and floating virus. Then, the resulting sterilized air may be transferred to the air supply member 200.

Figure 5A:
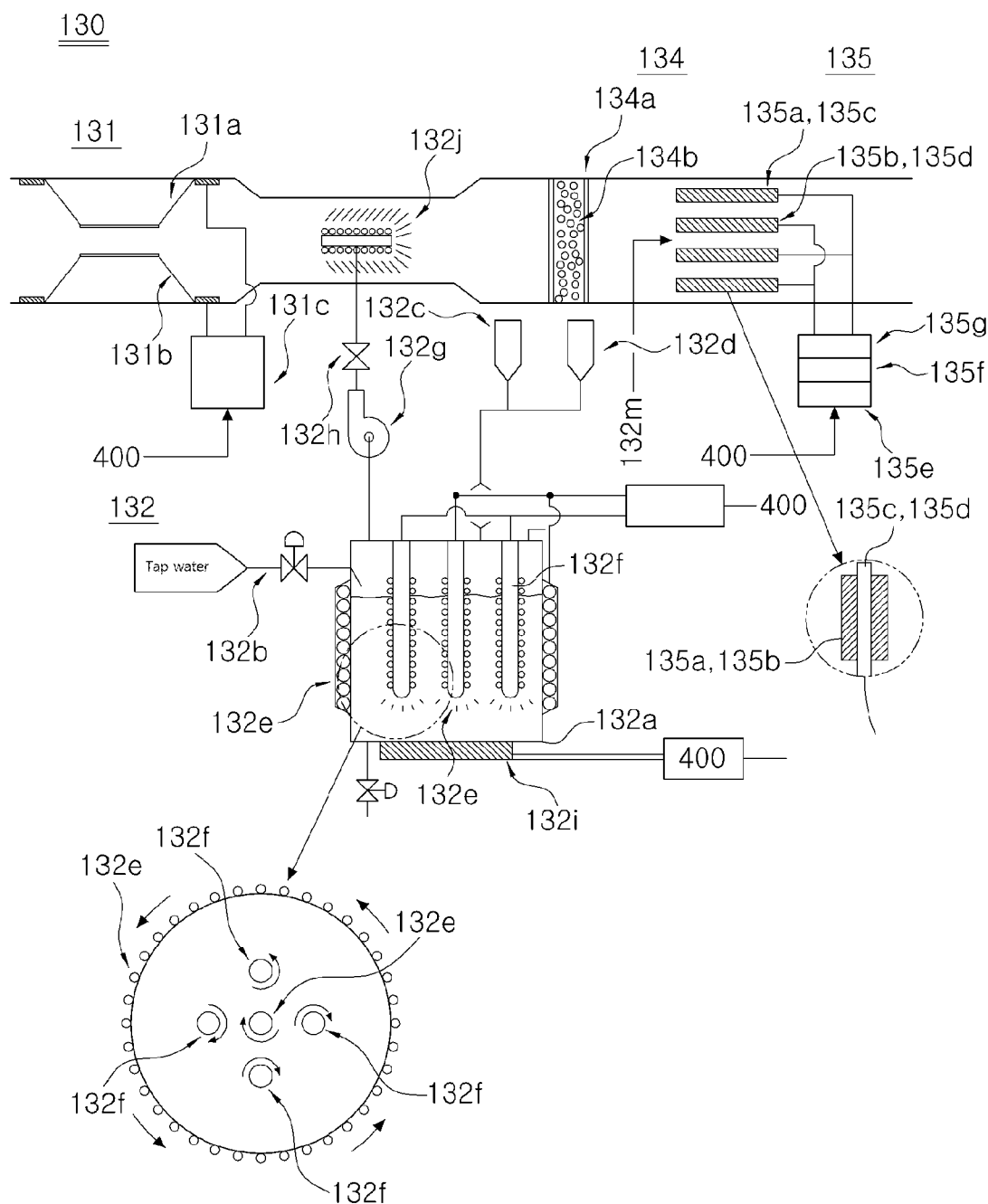
FIG. 5*a* is a partial sectional view showing a third preprocessing member illustrated in FIG. 2 in detail.
Figure 5B:
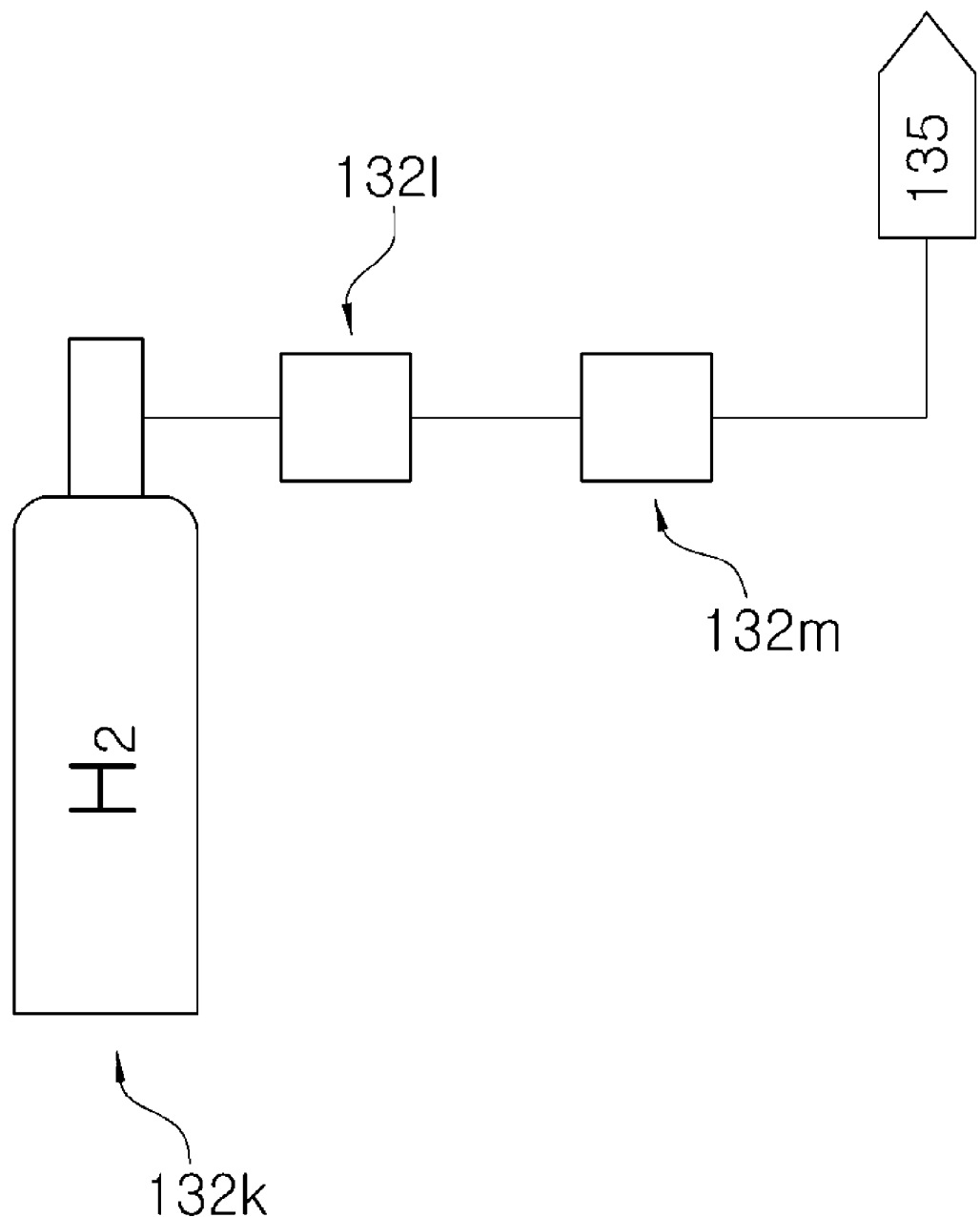
FIG. 5*b* is a partial sectional view showing another detailed configuration of a hydrogen supply member illustrated in FIG. 5*a*.

FIG. 5a is a partial sectional view showing a third preprocessing member illustrated in FIG. 2 in detail, and FIG. 5b is a partial sectional view showing another configuration of a hydrogen supply member illustrated in FIG. 5a in detail.

Referring to FIG. 5a, the third preprocessing member 130 may include the high-voltage discharge member 131, the hydrogen gas generator 132, the dehumidifying filter 134, and the electric adsorption portion 135, and thus may be applied to a preprocessing member of positive pressure equipment for emergency operating facilities (EOF) of nuclear power facilities and research facilities, nuclear power research facilities subject to the Laboratory Safety Management Act, and companies, institute research facilities and university research facilities, which use radiation.

The high-voltage discharge member 131 may include a discharge electrode 131a and a ground electrode 131b, which are installed to face each other inside the housing, and a high-voltage generator 131c, which supplies high voltage to the electrodes 131a and 131b through a conducting wire.

If the high-voltage discharge member 131 receives AC power from the control panel 400 and a high voltage generated from the high-voltage generator 131c is applied to the discharge electrode 131a and the ground electrode 131b through a conducting wire, a very high field electron energy band may be created to start discharge between two electrodes 131a and 131b. The polluted air containing harmful chemicals, which is introduced into the housing by a suction force of the air supply fan 211 of the air supply member 200, may pass between the electrodes 131a and 131b, during which high field electron energy formed between the electrodes 131a and 131b may be irradiated to the polluted air, so as to dissociate a covalent bond of hydrogen chloride (Hcl), chlorine ($Cl_2$), hydrogen fluoride (HF), formaldehyde (HCHO), acetaldehyde ($CH_3CHO$), toluene ($C_7H_8$), xylene ($C_8H_{10}$), ethylbenzene ($C_8H_{10}$) and styrene ($C_8H_8$) materials, thus resulting in ionization.

In addition, the high voltage generated by the high-voltage generator 131c may be applied to the electrodes 131a and 131b and the field electron energy generated between the electrodes 131a and 131b may be applied to primarily purify the contaminants in air through an electrochemical reaction such as dissociation, excitation, ionization, oxidation and reduction, so that the polluted air containing surplus contaminants in an ionic state may pass through the venturi portion installed in the main pipe and mixed with hydrogen gas which is generated by the hydrogen gas generator 132 and supplied to the venturi portion.

The hydrogen gas generator 132 may include a housing 132a, a tap water supply pipe 132b, an electrolyte supply portion 132c, an alkali metal powder supply portion 132d, a first solenoid coil 132e, a second solenoid coil 132f, a fan 132g, an electromagnetic valve 132h, a heating coil 132i, and an injection nozzle 132j, in which the electromagnetic valve of the tap water supply pipe installed at one side of a side surface of the housing 132a may be opened to supply a predetermined amount of tap water, and then shut off, after which the electromagnetic valve of the alkali metal powder supply portion 132d, which stores at least one material selected from magnesium, lithium, sodium, and potassium, may be opened, so that an appropriate amount of alkali metal powder may be inputted into the tap water and subject to reaction with the tap water to generate hydrogen gas. Then, the fan 132g may start running and the electromagnetic valve 132h will be opened to inject hydrogen gas through a nozzle installed inside the venturi portion.

In order to increase the amount of hydrogen generated, the electrolyte supply portion 132c may select at least one material from magnesium, lithium, sodium and potassium and supply an appropriate amount thereof to the inside of the housing by a gravitational difference.

The alkali metal powder that generates hydrogen is not limited to magnesium, lithium, sodium and potassium materials, but any material may be used as long as it generates hydrogen.

Among the above-described alkali metals, a preferred material in the present invention may be magnesium. When magnesium comes into contact with tap water, a reaction may be made as shown in Chemical Reaction Formula 1 below, in which magnesium hydroxide (($Mg(OH)_2$) may be generated and hydrogen gas ($H_2$) may occur.

$$MG + 2H_2O \rightarrow Mg(OH)_2 + H_2 \qquad \text{Chemical Reaction Formula 1}$$

The hydrogen gas generated by above Chemical Reaction Formula 1 and unreacted moisture may be pressurized by the fan and thus supplied to the injection nozzle 132j installed inside the venturi pipe.

To increase an amount of hydrogen generated inside the housing 132a, power may be supplied to the heating coil 132i installed inside the housing 132a by the control panel 400, so as to heat tap water or a mixed solution of electrolyte and tap water up to an appropriate temperature.

To increase an amount of hydrogen generated from a reaction between tap water and metal powder inside the housing 132a, the electrolyte supply portion 132c may store at least one material selected from the group consisting of potassium chloride, sodium chloride, calcium chloride, lithium chloride, potassium nitrate, sodium nitrate, potassium sulfate and a mixture thereof in a storage container, after which an electromagnetic value may be opened by a control circuit of the control panel 400, so that an appropriate amount thereof may be supplied into the housing 132a.

The first solenoid coil 132e and the second solenoid coil 132f may be installed at one side of both side surfaces of the housing 132a, and a magnetic field and quantum energy may be irradiated to alkali metal powder, tap water or a mixed solution of tap water and electrolyte inside the housing 132a, so as to promote hydrogen generation and activate the hydrogen gas generated.

The first solenoid coil 132e may have a coil having a predetermined diameter wound in the form of solenoid around an outer surface of the housing 132a and an outer surface of the fourth rod installed in the inner center of the housing 132a, and the second solenoid coil 132f may be installed at a distance from the first solenoid coil 132e of the fourth rod installed in the inner center of the housing 132a and also installed at a distance from an inner surface of the housing 132a, in which a coil having a predetermined diameter may be wound in the form of solenoid around an outer surface.

The winding directions of the first solenoid coil 132e and the second solenoid coil 132f may be opposite to each other. If the first solenoid coil 132e is wound in the clockwise direction by a certain number of turns, the second solenoid coil 132f may be wound in the counterclockwise direction. If the first solenoid coil 132e is wound in the counterclockwise direction by a certain number of turns, the second solenoid coil 132f may be wound in the clockwise direction.

If power of the same frequency, the same voltage and the same current is supplied to the first solenoid coil 132e and the second solenoid coil 132f in the control panel, the winding directions of the first solenoid coil 132e and the second solenoid coil 132f may be opposite to each other, thereby forming a magnetic field in the opposite direction. Accordingly, as the resulting magnetic fields are superimposed on each other and disappear, the total magnetic field may become zero. In reality, however, subtle energy (hereinafter, SE) may be generated. This SE may be also referred to as Scalar energy, non-Hertzian or the like as quantum energy, but in the present invention, it may be collectively referred to as a non-magnetic field energy (quantum energy) generation unit.

If power is supplied to the first solenoid coil 132e and the second solenoid coil 132f so as to apply a magnetic field generated in the direction perpendicular to the current flow direction, the electric field and the magnetic field may work and thus a mixed solution of tap water, electrolyte and alkali metal powder may flow inside the housing 132a by Lorentz force, thereby increasing an amount of hydrogen generated.

In addition, since the winding directions of the first solenoid coil 132e and the second solenoid coil 132f are formed in opposite directions to each other, if power is supplied, the magnetic fields generated in the direction perpendicular to the current flow direction may be generated in the directions opposite to each other, and the magnetic field in the first solenoid coil 132e and the second solenoid coil 132f as well as the Lorentz force acting on the magnetic field may work in the directions opposite to each other. Thus, the magnetic fields generated respectively between the first solenoid coil 132e and the second solenoid coil 132f may be superimposed on each other and the resulting SE may more activate the mixed solution of tap water, electrolyte and alkali metal powder.

The hydrogen gas generated by the hydrogen gas generator 132 and supplied to the nozzle of the venturi pipe may contain water vapor.

The mixed solution of tap water, electrolyte and alkali metal powder inside the housing 132a may be heated by the heating coil 132i, and a magnetic field and quantum energy may be irradiated, so that a part of the tap water of the mixed solution may be vaporized and mixed with the polluted air, which is introduced and supplied into the nozzle of the venturi pipe, along with hydrogen gas generated by a reaction between tap water and alkali metal powder, thereby adsorbing water-soluble radioactive contaminants such as radon isotope ($^{222}$Rn), etc., in the polluted air.

If magnesium balls come into contact with moisture, magnesium hydroxide (($Mg(OH)_2$) may be generated and hydrogen gas ($H_2$) may be generated as shown in Chemical Reaction Formula 1 below.

$$MG + 2H_2O \rightarrow Mg(OH)_2 + H_2$$    Chemical Reaction Formula 1

Hydrogen gas generated by above Chemical Reaction Formula 1 and unreacted moisture may be contained in air and introduced into a dehumidifying filter 134 installed at a pipeline by a suction force of the air supply fan 211 of the air supply member 200.

In addition, a member for supplying hydrogen gas to the electric adsorption portion 135 may include a hydrogen gas bombe 132k filled with hydrogen gas, a pressure reducer 132l, a flow control valve 132m and supply pipe 132n as shown in FIG. 5b, so that the pressure reducer 132l may decompress hydrogen gas filled at a high pressure (100 atmospheres) in the range of 20 to 100 mmAq and supply to the electric adsorption portion 135.

The dehumidifying filter 134 may include a dehumidifying agent 134b filled into a cage 134a, in which a plurality of holes having a diameter in the range of 2 mm to 5 mm are formed on an outer surface thereof. The dehumidifying agent 134b may include at least one material selected from inorganic matters such as porous silica gel, activated alumina, diatomaceous earth, etc., superabsorbent polymers such as an acrylic acid crosslinked polymer, an acrylamide crosslinked polymer, and acrylic acid/amide weakly crosslinked polymer, etc., deliquescent inorganic matters such as calcium chloride, magnesium chloride, potassium sulfate, magnesium sulfate, etc., may dehumidify the moisture in the air mixed with the hydrogen gas containing water vapor so that an indoor relative humidity (RH) may be maintained in the range of 55% to 65%. The air dehumidified by the dehumidifying filter 134 may be introduced into the electric adsorption portion 135, which is installed at a distance from the dehumidifying filter 134, by a suction force of the air supply fan 211 of the air supply member 200.

The electric adsorption portion 135 may include ion exchange resin layers 135a and 135b, a discharge electrode 135c and a ground electrode 135d, a transformer 135e which decompresses the AC power of 220V, 60 Hz to the AC power of 60V to 100V, 60 Hz, a rectifier 135f with a built-in rectifier circuit which converts AC power to DC power, and converter 135g which converts a polarity of DC power supplied to the electrodes 135c and 135d at every time set to a timer (not shown).

The ion exchange resin layers 135a and 135b of the electric adsorption portion 135 may be so configured that the ion exchange resin layers 135a and 135b having a thickness of 3 mm to 20 mm are coated on a surface of the discharge electrode 135c and the ground electrode 135d. An ion exchange resin material coated on an outer surface of the electrodes 135c and 135d may include any one selected from a chelate resin having a phosphono group as a functional group, an anion exchange resin, a cation exchange resin, and a titania-based absorbent resin, in which the ion exchange resin may include a chelate resin containing a phosphono group as a functional group, sulfonated poly(ethylene)-lignin combined type chelate resin, iminodiacetic acid resin, nitrilotriacetic acid resin, dithiocarbamic acid group-containing chelate resin, phosphinoacetic acid resin, thiourea resin, picolylamine resin, sulfonamide type chelate resin, quaternary amine resin, tertiary amine resin, titania-based absorbent resin, aminoalkylpropinic acid resin, aminodiacetic acid resin, aromatic amine resin, thiol resin, sulfonated phonol resin, and a mixture thereof. In particular, a preferred ion exchange resin may be coated with at least one selected from iminodiacetic acid resin, thiourea resin, quaternary amine resin, thiol resin, titania-based absorbent resin, hydrophilic polyurethane resin, hydrophilic polyurea resin, hydrophilic polyurethane-urea resin, and a mixture thereof.

The chelate resin containing the phosphono group as a functional group and the quaternary amine resin may be useful in removing uranium ($^{234,238}$U) and the quaternary amine ion exchange resin may be useful for removing lead ($^{210}$Pb) and polonium ($^{210}$,$^{218}$Po). Aminoalkylpropinic acid resin and aminodiacetic acid resin may be useful for adsorbing strontium.

Hydrophilic polyurethane resin, hydrophilic polyurea resin, and hydrophilic polyurethane-urea resin may be useful for adsorbing cesium (CS) and radioactive iodine.

In addition, with regard to a variety of resins described above, at least one material selected from layered clay materials such as smectite, kaolinite, montmorillonite, bentonite, hectorite, hectorite fluoride, beidellite, saponite, nontronite, vermiculite, makatite, sericite, mica, etc., may be combined with alginate or sodium alginate, mixed in a resin layer, and used as an adsorbing agent for cesium (CS) such as $^{137}$CS, $^{135}$CS, $^{134}$CS, etc.

However, it is impossible to detailedly figure out the kind and concentration of radiation-emitting materials emitted from each nuclear power plant or semiconductor and electronic business site. Thus, in the present invention, the electrodes 135c and 135d coated with the ion exchange resin layers 135a and 135b may be prepared by uniformly mixing an anion exchange resin, a cation exchange resin, and a titania-based absorbent resin, having absorption performance for a specific radiation-emitting material. Alternately, if the kind of radiation-emitting materials and the emission amount thereof are identified, the above electrodes may be prepared by combining the above ion exchange resins in an order of descending amount of emissions, adding adhesive polyvinyl alcohol to a mold (not shown), which is prepared to have the same area as that of the electrodes 135c and 135d, and pressing the resulting mold with a hydraulic press (not shown).

It is preferable that the above-described electrodes 135c and 135d have a cuboid shape and include at least one material selected from platinum, palladium, titanium, aluminum, copper, stainless steel, carbon, etc. And, the ion exchange resin may be bonded to the electrodes 135c and 135d in such a way that the upper and lower molds (not shown) having a tolerance of 1 to 2 mm in an area of the electrodes 135c and 135d may be mounted onto a hydraulic press (not shown), after which a prepared ion exchange resin plate may be applied onto the floor of the lower mold, and then an adhesive such as polyvinyl alcohol, etc., may be applied thereon, so that the electrodes 135c and 135d may be uniformly aligned with the ion exchange resin plate, and then the hydraulic press may be activated to lower and press the upper mold mounted on the hydraulic press. After that, the process opposite surface may be prepared through compression by the same method, after which the completed electrodes 135c and 135d may be mounted on the internal cradle (not shown) of the electric adsorption portion 135.

The power supply system for supplying power to the electrodes 135c and 135d of the electric adsorption portion 135 may include a variable step-up transformer 135e configured to select a specific volt (V) in the range of 1 KV to 50 KV for AC power of 220V 60 Hz, also select a specific frequency in the range of 60 Hz to 20 KHz for the frequency, and boost a voltage to AC power, and a rectifier 135f having a built-in rectifier circuit configured to convert AC power into DC power, and a polarity converter 135g configured to convert a polarity of DC power to be supplied to the electrodes 135c and 135d at every time set in a timer (not shown), in which an AC power supply line of the control panel 400 may be connected to an input side of the transformer 135e, a conducting wire in an output side of the transformer 135e may be connected to an input side of the rectifier 135f, a conducting wire of an output side of the rectifier 135f may be connected to an input side of the polarity converter 135g, and a conducting wire of an output side the polarity converter 135g may be connected to a plurality of discharge electrodes (positive pole: 135c) and ground electrodes (negative pole: 135d) installed in an internal cradle, respectively so as to supply power.

The radiation-emitting material and the hydrogen gas, which are introduced into the electric adsorption portion 135 by a suction force of the air supply fan 211 of the air supply member 200, may be adsorbed onto resin layers 135a and 135b, which are formed in such a way that any one resin may be selected from a chelate resin having a phosphono group as a functional group, an anion exchange resin, a cation exchange resin, and a titania-based absorbent resin, and at least one material selected from layered clay materials such as smectite, kaolinite, montmorillonite, bentonite, hectorite, hectorite fluoride, beidellite, saponite, nontronite, vermiculite, makatite, mica, etc., may be combined with alginate, mixed with the resin layer described above, and coated on the resin layers 135a and 135b. Then, the resulting radiation-emitting material and the hydrogen gas may be subject to a first oxidation reaction with the functional group (phosphono group) contained in the resin and adsorbed onto an adsorbing agent such as hectorite. Then, if the control panel 400 applies AC power of 220V, 60 Hz to an input side of a variable step-up transformer 135e, AC power, which is inputted according to a number of coil turns inside the step-up transformer 135e, may be boosted to AC power of 1 KV to 50 KV and applied to an input side of the rectifier 135f, and then may be converted into DC power of voltage 1 KV to 50 KV in a built-in rectifier circuit and applied to an input side of a polarity converter 135g, so that a polarity of the output side may change from a positive power to a negative power or a negative power to a positive power at every time set in a timer (not shown) mounted inside the polarity converter 135g, and applied to the discharge electrode 135c and the ground electrode 135d, which may use at least one selected from platinum, palladium, titanium, aluminum, copper, stainless steel, carbon, etc., so as to start discharge. The hydrogen gas, which is introduced between the electrodes 135c and 135d, may be dissociated into a hydrogen atom (H), so as to remove the reactive materials such as lead isotope ($^{210}$Pb), cesium (CS), uranium isotope ($^{234}$, $^{238}$U), thorium isotope ($^{230}$Th), radium isotope ($^{226}$Ra), radon isotope ($^{222}$Rn), polonium isotope ($^{210}$, $^{218}$Po), lead isotope ($^{210}$Pb), etc., which are attached onto the ion exchange resin layers 135a and 135b, through a reduction reaction. Accordingly, hydrogen gas, which is a reducing ion, may treat the radiation-emitting materials attached onto a surface of the ion exchange resin layers 135a and 135b in the following process.

(1) Dissociable attachment: $H_2 + e- \rightarrow H- + H$
(2) Electron attachment: $e- + H \rightarrow H- + hY$
(3) Combination of the (1) and (2) processes: Electron attachment: $2e- + H_2 \rightarrow 2H- + hY$
(4) Reduction of oxides: $2H- + MO \rightarrow M + H_2O + 2e-$
(M-Radiation-Emitting Material)

In the specific embodiment as above, the activation energy for reduction of oxides may be lower than that of the method using hydrogen molecules. That's because the formation of hydrogen atom ions through electron attachment may eliminate the energy associated with breaking the bond of hydrogen molecules.

Energy (DC power) enough to generate electrons from the gaseous phase (introduced air) between the discharge electrode (positive pole: 135c) and the ground electrode (negative pole: 135d) may be supplied to the positive pole (in this case, the negative pole is grounded).

In addition, the source for energy may be pulsed to make electron generation constant or to generate a large amount of electrons. In addition, the voltage applied to the discharge electrode (positive pole: 135c) and the ground electrode (negative pole: 135d) may be supplied by 1 KV-10 KV higher than the voltage applied to the ground electrode (negative pole: 135d), thus resulting in a voltage difference and a bias at the electric potential. The electrons generated from the discharge electrode 135a may be then drifted from the discharge electrode (positive pole: 135c) to the ground electrode (negative pole: 135d) forming space charge. The space charge may serve as a source for generating negatively charged ions when hydrogen, which is a reducing gas, passes through the two poles of the discharge electrode (positive pole: 135c) and the ground electrode (negative pole: 135d).

However, there are cases where negatively charged ions are neutralized at the ground electrode (negative pole: 135d). To prevent this neutralization, a part of an upper layer of the ground electrode (negative pole: 135d) may be coated with a ceramic material or a solenoid coil 135h may be wound by a predetermined number of turns around an outer portion of the electric adsorption portion 135, after which power may be supplied to the wound coil 135h by the control panel 400 to generate a magnetic field of 3000 to 15,000 gauss, and restrict the movement of electrons in the electric adsorption portion 135, thereby preventing the neutralization of negatively charged ions at the ground electrode (negative pole: 135d). Thus, a reduction action of the radiation-emitting materials may be constantly performed.

In addition, in the process described above, the radiation-emitting materials may serve as a source of supplying electrons, in such a way that hydrogen, which is a reducing gas, may be generated through a contact reaction between the injected moisture and magnesium, the generated hydrogen gas may pass through the discharge electrode (positive pole: 135c) and the ground electrode (negative pole: 135d), to which high voltage is applied, and hydrogen molecules may be dissociated into hydrogen atoms to generate the negatively charged ions, thereby reducing and removing a variety of oxides adsorbed to the ion exchange resins 135a and 135b. The air, from which bacteria are sterilized and harmful materials and radioactive materials are removed by the preprocessing unit 100, may be transmitted to the air supply member 200 by a suction force of the air supply fan 211.

Figure 6:
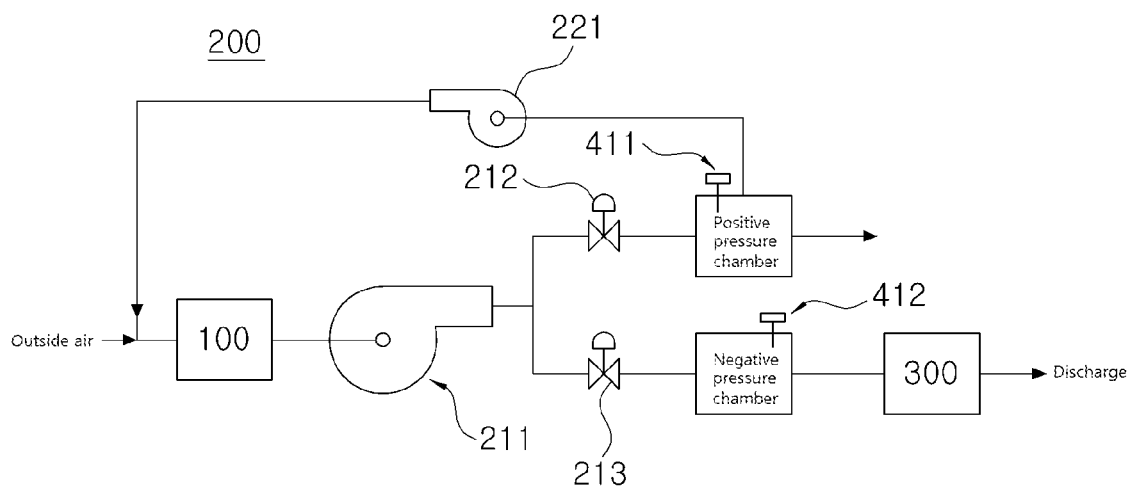
FIG. 6 is a view showing a detailed configuration of an air supply member illustrated in FIG. 1.

FIG. 6 is a view showing a detailed configuration of an air supply member illustrated in FIG. 1.

Referring to FIG. 6, the air supply member 200 may include an air supply fan 211, a positive pressure chamber air flow control damper 212, a negative pressure chamber air flow control damper 213 and a main pipe 214. The air supply member 200 may supply purified air into a positive pressure chamber and a negative pressure chamber at the same time with the single air supply fan 211.

An indoor pressure of the positive pressure chamber may be adjusted by activating the air supply fan 211 to open the air volume control damper 212 of the positive pressure chamber in the main pipe 214 connected to the positive pressure chamber. Then, if air is continuously supplied into the positive pressure chamber, a part of air may be discharged through a gap in a door to gradually increase an indoor pressure. In this case, a detection sensor 411 of the positive pressure chamber, installed at one side indoors, may measure an indoor pressure in real time and transmit the measured data to the control panel 400. If a set value (2.5 Pa to 25 Pa) is satisfied according to a control circuit, which is programmed and inputted in advance, the control panel 400 may decrease a number of rotations of the air supply fan 211 to reduce an amount of air to be supplied into the positive pressure chamber. If an indoor pressure transmitted from the detection sensor 411 of the positive pressure chamber fails to satisfy the set value, the control panel may increase a number of rotations of the air supply fan 211 to raise an amount of air to be supplied into the positive pressure chamber, thereby maintaining the indoor pressure in the range of the set value. With regard to controlling an air volume by adjusting the number of rotations of the air supply fan 211, it may be suitable to control an air volume by 10 to 50% of the rated air volume of the air supply fan 211. With regard to controlling a micro-air volume, it may take a certain time to adjust a micro-pressure indoors by supplying a micro-air volume into the positive pressure chamber due to inertial force of wings of the air supply fan 211.

In addition, since a configuration of the control circuit is complex and a cost of equipment rises, the present invention may adopt a dual control method, which includes the air supply fan 211 and the air volume control damper 212 of the positive pressure chamber, in which the air volume control damper 212 of the positive pressure chamber may be installed at one side of the main pipe 214 connected with the positive pressure chamber so as to adjust an amount of air to be supplied into the positive pressure chamber. An air volume may be adjusted in the range of 10 to 50% of an entire air volume of the adopted air supply fan 211 by adjusting a number of rotations of the air supply fan 211 and a micro-air volume may be adjusted by adjusting an opening rate of the air volume control damper 212, so as to promptly maintain an indoor pressure at a set value in the positive pressure chamber, if the indoor pressure departs from the set value.

An indoor pressure of the negative pressure chamber may be maintained in the range of −2.5 Pa to −11 Pa in such a way that the air supply fan 211 may be operated to open the air volume control chamber 213 of the negative pressure chamber in the main pipe 214 connected to the negative pressure chamber, after which air may be continuously supplied into the negative pressure chamber and discharged outside by using the discharge fan 311 of the postprocessing unit 300 installed at one side of an upper part of the negative pressure chamber. If the indoor pressure gradually rises and departs from a set value, the detection sensor 412 of the negative pressure chamber installed at one side of the room may measure the indoor pressure in real time and transmit the measured data to the control panel 400. If the indoor pressure satisfies a set value (−2.5 Pa to −11 Pa), the control panel 400 may lower down the number of rotations of the air supply fan 211 to decrease an amount of air to be supplied into the negative pressure chamber according to a control circuit which is programmed and inputted in advance, or reduce an opening rate of the air volume control damper 213 of the negative pressure chamber at one side of the main pipe 214 to adjust an amount of air to be supplied into the negative pressure chamber, or increase a number of rotations of the air supply fan 311 of the postprocessing unit 300 to maintain the indoor pressure within the range of set value.

The air supply fan 211 may include any one fan selected from a multi-blade fan (SIROCCO FAN), an airfoil fan (AIRFOIL FAN) and a turbo fan (TURBO FAN), in which the multi-blade fan (SIROCCO FAN) may be applied to a space in which a positive pressure is to be maintained at 2.5 Pa to 8.0 Pa, or may be used in a space in which a negative pressure is to be maintained at −2.5 Pa to −11.0 Pa, and the airfoil fan (AIRFOIL FAN) or the turbo fan (TURBO FAN)

may be applied to a space in which a positive pressure is to be maintained at 25 Pa to 250 Pa.

In addition, in case of a positive/negative pressure maintenance system to be applied to a control panel of a factory using flammable and combustible materials or a special-purpose vehicle, air for maintaining a positive/negative pressure may be supplied to the space in which the positive/negative pressure is to be maintained through one air supply fan 211, while a separate positive pressure maintenance system may be built in a driver's cabin. Furthermore, in case of the space in which the positive pressure is to be maintained, it may be easy to maintain the positive pressure at 25 Pa or more by adjusting an air volume to be supplied into the space in which the positive pressure is to be maintained to be larger than an air volume to be supplied into the space in which the negative pressure is to be maintained. In case of the space in which the negative pressure is to be maintained, an opening rate of the air volume control damper 212 of the positive pressure chamber installed in the main pipe 214 connected with the positive pressure chamber may be adjusted to be larger than an opening rate of the air volume control damper 213 of the negative pressure chamber installed in the main pipe 214 connected with the negative pressure chamber, so that an amount of air discharge may be easily adjusted and thus the negative pressure may be also easily maintained with an indoor pressure in the range of −2.5 Pa to −11.0 Pa.

Furthermore, in case of a large space in which the positive pressure is to be maintained like a clean room of semiconductor and pharmaceutical sectors, government dissipation facilities and CBR facilities, a full air supply and full discharge-type positive pressure maintenance system may require a large amount of energy loss. Thus, a separate circulation pipe 222 attached with the circulation fan 221 may be installed therein to supply and circulate by 65% to 85% of a total amount of air supply to be supplied into the space in which the positive pressure is to be maintained toward one side of the housing 101 of an air inlet while satisfying conditions for positive pressure indoors. Thus, it may be possible to save energy for heating in winter season and energy for cooling in summer time.

Moreover, a method for maintaining a positive pressure and a negative pressure set to a space in which the positive pressure is to be maintained and a space in which the negative pressure is to be maintained may include a method in which an air volume and voltage of the air supply fan 211 and the discharge fan 311 of the negative pressure chamber may be adjusted by increasing or decreasing a number of rotations of the air fan 211 and the discharge fan 311 of the negative pressure chamber by using an inverter control circuit based on a micro-current value in the range of 4 mmA to 20 mmA which may be transmitted from the detection sensor 411 of the positive pressure chamber to the control panel 400, and a method in which an opening rate of an electromotive damper may be increased or decreased by using a proportional-integral-derivative control circuit (PID Control) based on a micro-current value in the range of 4 mmA to 20 mmA which may be transmitted from the detection sensors 411 and 412 to the control panel 400.

According to the method for adjusting the number of rotations of the air fan 211, the circulation fan 221 and the discharge fan 311 by using the inverter control circuit, the detection sensor 411 of the positive pressure room and the detection sensor 412 of the negative pressure room may be installed in the space in which the positive/negative pressures are to be maintained. In case of the condition for positive pressure maintenance according to a control program, which is programmed and inputted in advance based on data measured in real time from the sensors and transmitted to the control panel 400, the pressure of the target space may be maintained at a reference value for positive pressure or negative pressure thereof in such a way that the number of rotations (RPM) of the motor of the air supply fan 211 may become larger than the RPM of the motor of the circulation fan 221 or the discharge fan 311 of the negative pressure chamber. In case of the condition for negative pressure maintenance, the pressure of the target space may be maintained at a reference value for positive pressure or negative pressure thereof in such a way that the RPM of the motor of the discharge fan 311 of the negative pressure chamber may become larger than the RPM of the motor of the air supply fan 211. In this case, a law of similarity for an air blower may be applied to the method for maintaining the positive pressure and the negative pressure by adjusting the RPM of the motor of the air supply fan 211 and the RPM of the circulation fan 221 or the discharge fan 311, which may be one of the methods for satisfying conditions for maintaining the positive pressure and the negative pressure.

A law of similarity for an air blower may be the same as shown in following formulas 1, 2, 3, 4, 5 and 6.

1. Relation Between RPM of Fan and Air Volume (m3/Min)

$$\text{Condition for positive pressure maintenance: } Q1(N1) > Q2(N2) \quad \text{Formula 1}$$

$$\text{Condition for negative pressure maintenance: } Q1(N1) > Q3(N3) \quad \text{Formula 2}$$

In this case, Q1(N1): Air volume (m3/min) and RPM of air supply fan 211

Q2(N2): Air volume (m3/min) and RPM of circulation fan 221

Q3(N3): Air volume (m3/min) and RPM of discharge fan 311

The law of similarity for an air blower may be applied to above formulas 1 and 2 and an air volume may be proportional to the first power of a change in the number of rotations.

2. Relation Between RPM of Fan and Air Pressure (Mmaq)

$$\text{Condition for positive pressure maintenance: } PS1(N1)^2 > PS2(N2)^2 \quad \text{Formula 3}$$

$$\text{Condition for negative pressure maintenance: } PS1(N1)^2 > PS3(N3)^2 \quad \text{Formula 4}$$

In this case, $PS1(N1)^2$: Air pressure (mmaq) and RPM of air supply fan 211

$PS2(N2)^2$: Air pressure (mmaq) and RPM of circulation fan 221

$PS3(N3)^2$: Air pressure (mmaq) and RPM of discharge fan 311

The law of similarity for an air blower may be applied to above formulas 3 and 4 and an air pressure may be proportional to the second power of a change in the number of rotations.

3. Relation Between RPM of Fan and Shaft Power (Hp) of Fan $$\text{Condition for positive pressure maintenance: } Hp1(N1)^3 > Hp2(N2)^3 \quad \text{Formula 5}$$

$$\text{Condition for negative pressure maintenance: } Hp1(N1)^3 > Hp3(N3)^3 \quad \text{Formula 6}$$

In this case, $Hp1(N1)^3$: Shaft power (Hp) and RPM of air supply fan 211

Hp2(N2)$^3$: Shaft power (Hp) and RPM of circulation fan 221

Hp3(N3)$^3$: Shaft power (Hp) and RPM of discharge fan 311

The law of similarity for an air blower may be applied to above formulas 5 and 6 and a shaft power may be proportional to the third power of a change in the number of rotations.

As above, an indoor pressure of the positive pressure chamber and the negative pressure chamber may be adjusted by using an air volume control method of adjusting a number of rotations of the fans 211, 221 and 311 using a proportional-integral-derivative control circuit (PID Control) based on a micro-current value in the range of 4 mmA to 20 mmA that is transmitted to the control panel 400 by the detection sensors 411 and 412, and may be adjusted by adjusting an opening rate of air volume control dampers 212 and 213 and adjusting an amount of air supplied.

In addition, in case of a small space in which the positive pressure is to be maintained, the positive pressure may be maintained by supplying outside air into the space in which the positive pressure is to be maintained through the air supply fan 211, and by using a gap in an entrance door and a window frame in a discharge form. When an amount of discharge is temporarily increased by opening the entrance door or the window so as to decrease an indoor pressure at a set pressure value or less, the indoor pressure may be maintained at the set value by adjusting a number of rotations of the air supply fan 211 and adjusting an opening rate of the air volume control dampers 212 and 213 according to data which is measured by the detection sensor 411 and transmitted to the control panel 400.

Furthermore, if the air supply fan 211 and the air volume control dampers 212 and 213 of the air supply member 200 as well as the discharge fan 321 of the postprocessing unit 300 are installed in explosion hazardous areas of "Class 0", "Class 1", and "Class 2", where an explosive atmosphere is created due to combustible gases, etc., a motor of the fans 211 and 321 and the air volume control damper 212 and 213 may cause a spark from a brush portion and a contact portion when starting or stopping the positive pressure and negative pressure maintenance system and this spark may serve as a source of ignition among fire and explosion factors, and thus the motor may be formed by selecting at least one of an explosion-proof structure for internal pressure (d, flameproof enclosure), an increased safety explosion-proof structure (e, increased safety), an intrinsic safety explosion-proof structure (i, intrinsic safety), and a pressurization explosion-proof structure (p, pressurization).

Furthermore, a motor of the fans 211 and 321 and the air volume control dampers 212 and 213, which may be installed in places classified as "Class 20", "Class 21", and "Class 22" where an explosive atmosphere is created due to combustible dusts, etc., may be formed by selecting at least one suitable explosion-proof structure out of "dust explosion-proof structure for internal pressure (tD)," "dust mold explosion-proof structure (mD)," "dust intrinsic safety explosion-proof structure (iD)," and "dust pressure explosion-proof structure (pD)."

Moreover, a material of a casing of the fans 211 and 321 may have a non-spark material performance in such a way that any one material may be selected from non-spark materials such as PVC, FRP (glass fiber molding foam), carbon fiber molding foam, etc., one material of a blade of the fans 211 and 311 may be selected from copper or copper alloy, duralumin or aluminum alloy, and the FRP may be coated by a certain thickness or more on a surface of steel and stainless steel (STS304).

The reason for selecting and adopting the non-spark material for the casing and the blade of the fans 211 and 311 described above may be that, if a bearing inserted into a rotational shaft is worn and damaged, a blade rotating in connection with the rotational shaft inside the casing may break away due to the damaged bearing or may collide with an interior of the casing and cause a scratch phenomenon due to an abnormal rotation, and may cause a spark in case of a general metal material. Then, if inflammable gas, combustible gas and combustible dust exceeding an explosion lower limit are introduced into the casing of the fans 211 and 311, the spark caused by the collision and the scratch phenomenon may serve as a source of ignition. Thus, the casing and the blade may be made of the non-spark material in order to prevent any fire and explosion.

Figure 7:
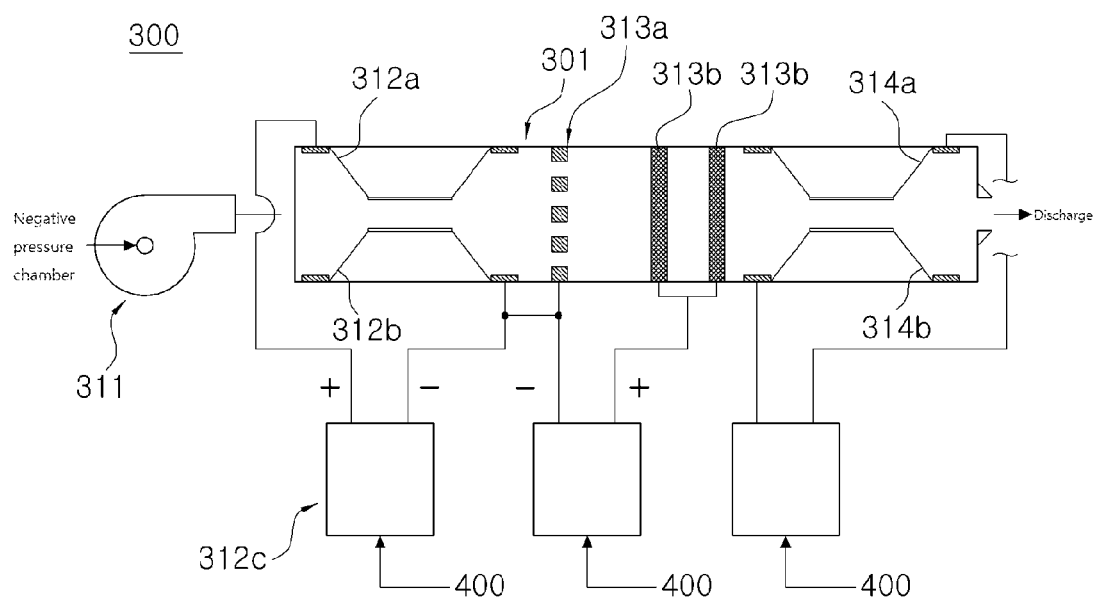
FIG. 7 is a view showing a detailed configuration of a postprocessing unit illustrated in FIG. 1.
Figure 8:
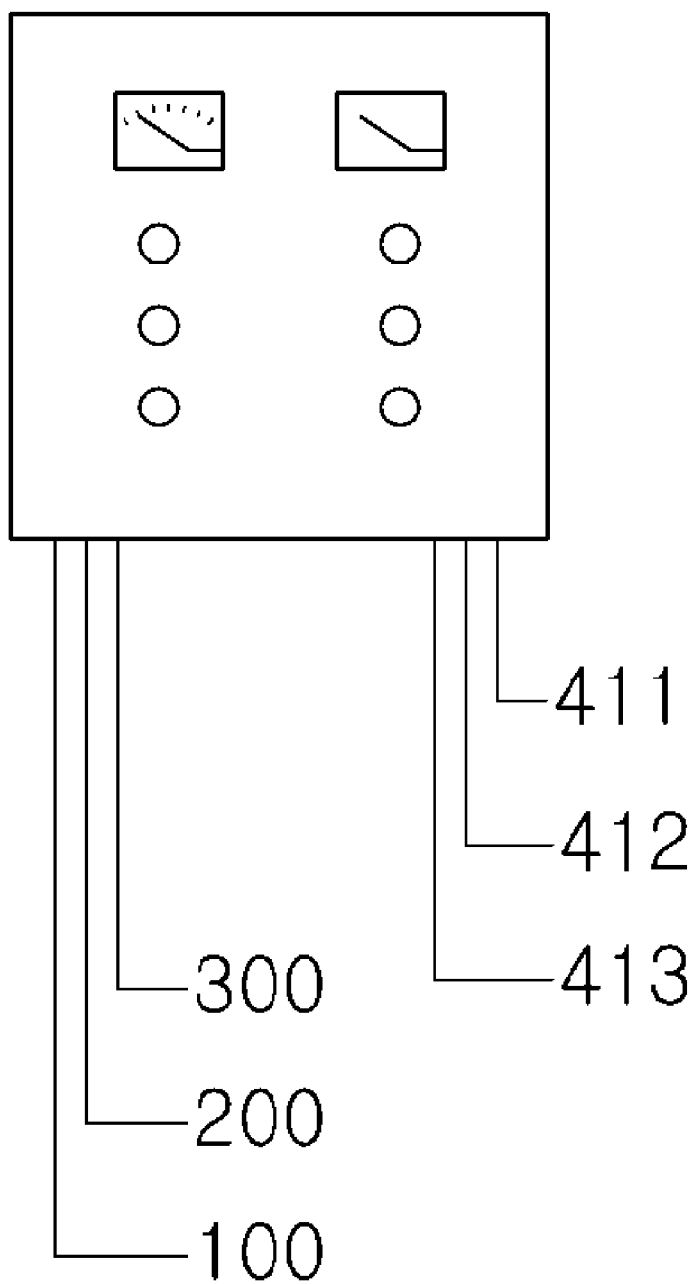
FIG. 8 is a view showing a configuration of a control panel according to a preferred embodiment of the present invention.

FIG. 7 is a view showing a detailed configuration of a postprocessing unit illustrated in FIG. 1, and FIG. 8 is a view showing a configuration of a control panel according to a preferred embodiment of the present invention.

Referring to FIGS. 7 and 8, the postprocessing unit 300 may include a discharge fan 311, an air volume control damper (not shown), a first high-voltage discharge member 312, an adsorption member 313 and a second high-voltage discharge member 314, and may be connected to one side of an upper portion of or a part of a side surface of the negative pressure chamber. The control panel 400 of the postprocessing unit 300 may be separately and independently installed or the control panel 400 of the positive pressure maintenance system may be used.

The first high-voltage discharge member 312 may include a housing 301, a discharge electrode 312a and a ground electrode 312b, which are installed to face each other inside the housing 301, and a high-voltage generator 312c, which supplies DC high voltage to the electrodes 312a and 312b through a conducting wire. If AC power is received from the control panel 400 and a high voltage generated from the high-voltage generator 312c is applied to the discharge electrode 312a and the ground electrode 312b through a conducting wire, a very high field electron energy band may be created to start discharge between two electrodes 312a and 312b.

A positive pole of the high-voltage generator 312c may be connected to the discharge electrode 312a, and a negative pole of the high-voltage generator 312c may be connected to the ground electrode 312b and then connected to a grid 313a of the adsorption member so as to form a bias voltage.

The polluted air containing harmful chemicals, bacteria and viruses in the negative pressure chamber may pass between the electrodes 312a and 312b by a suction force of the discharge fan 311, during which high field electron energy formed between the electrodes may be irradiated to the polluted air, so as to dissociate a covalent bond of chlorohexidine gluconate, which is an antiseptic for disinfecting hand and skin and disinfecting a surgical site, isopropyl alcohol, which is a hand sanitizer, and besetine solution (volatilized vapor), which is an antiseptic for torn wound, burn, ulcer and abscess, resulting in ionization.

In addition, the high voltage generated by the high-voltage generator 312c may be applied to the electrodes 312a and 312b and the field electron energy generated between the electrodes may be applied to primarily purify the contaminants in air through an electrochemical reaction such as dissociation, excitation, ionization, oxidation and reduction, so that the polluted air containing surplus contaminants in an ionic state may be transferred to the adsorption member 313 installed at a distance.

The adsorption member 313 may include a grid 313a, a cage 313b, a DC power supply 313c, a conducting wire 313d, and an adsorption material 313e, and the grid 313a may be made of a metal material of stainless steel, in which a plurality of holes having a predetermined diameter are formed, and may be connected to a negative pole of the DC power supply 313c and connected to the ground electrode 312b of the first high-voltage discharge member 312.

The cage 313b may be made of a metal material of stainless steel in which a plurality of holes having a predetermined diameter are formed on an outer surface thereof and may include a cuboid shape. The adsorption material 313e for adsorbing chlorohexidine gluconate, isopropyl alcohol and besetine solution (volatilized vapor) may include at least one material selected from zeolite (ZSM-5, ZSM-8) mixed with globular conductive activated carbon, activated alumina mixed with conductive activated carbon, or pellet-type activated carbon and may be filled into a cage 313b without a separate carrier. Then, if power is supplied to a DC power supply 313c through the control panel 400 while a primarily purified air is introduced in a process of high-voltage discharge of the first high-voltage discharge member 312, repulsive force may work in the grid (negative pole) 313a and be applied to ionic materials produced in a process of discharge of the high-voltage discharge portion so as to disturb a flow of the ion materials, thereby extending a retention time, enhancing a reaction efficiency between unreacted contaminants and ion materials, and improving contact efficiency between contaminants and ion materials while passing through a plurality of holes having a predetermined diameter in the grid.

Also, attractive force may work between the case connected to a positive pole of the DC power supply and the conductive activated carbon carrier filled inside the case, so as to attract the ionized contaminants to the carrier and the adsorbing agent by electrical attractive force, thereby enhancing adsorption efficiency. The air purified with harmful gases adsorbed by the harmful material adsorption member may be transferred to the second high-voltage discharge member 314, in which the second high-voltage discharge member 314 may include a housing 301, a discharge electrode 314a and a ground electrode 314b, which may be installed to face each other inside the housing, and a high-voltage generator 342c configured to supply high voltage to electrodes 314a and 314b through a conducting wire. If AC power is received from the control panel 400 and the high voltage generated from the high-voltage generator 342c is applied to the discharge electrode 314a and the ground electrode 314b through a conducting wire, a very high field electron energy band may be created between two electrodes 314a and 314b to start discharge, so that the resulting air may be purified in the first high-voltage discharge member 312 and the adsorption member 313 and then introduced into the second high-voltage discharge member 314, thereby attacking a cellular wall of bacteria such as fungi, *Pseudomonas aeruginosa, Staphylococcus aureus*, pneumococcus, *Legionella*, etc., and floating viruses such as variant virus (MRSA), MERS coronavirus (MERS-COV), Ebola virus, Sascorona virus (SARS-COV), bacteria, etc., in the introduced air, with free radicals such as superoxide anion (O2-), hydroxyl radical (OH-radical), nitrogen monoxide (NO), singlet oxygen (102), etc., including an active radical such as hydroxyl radical (OH-radical), in which an oxygen ion (O) generated by dissociating an oxygen molecule (O2), a nitrogen molecule (N2) and a water molecule (H2O) of water vapor, which are introduced into the second high-voltage discharge member 314, may be bonded with oxygen in an unstable form, resulting in decomposition and perforation of the cellular wall, damage to biological tissues and organs, and sterilization of bacteria and floating viruses, thereby discharging the sterilized air to block a path of spreading infectious bacteria and viruses with air as a medium and preventing a spread of viruses and health harmfulness.

Figure 9:
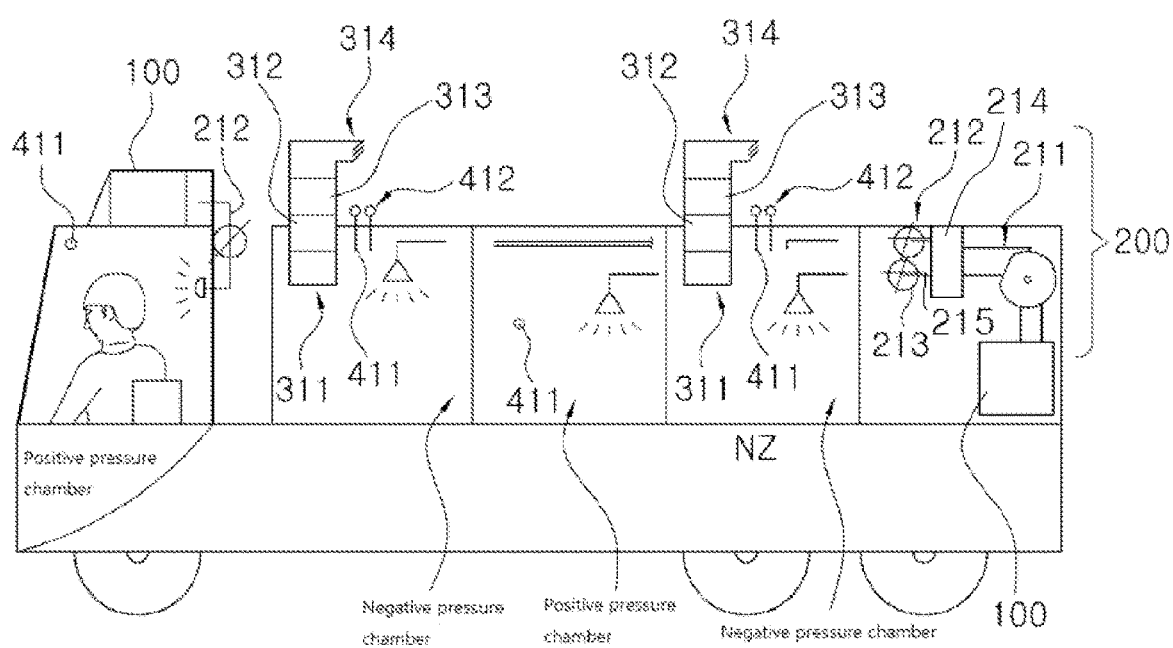
FIG. 9 is an exemplary view showing a special-purpose vehicle, to which the positive pressure and negative pressure maintenance system according to a preferred embodiment of the present invention is applied.
Figure 10:
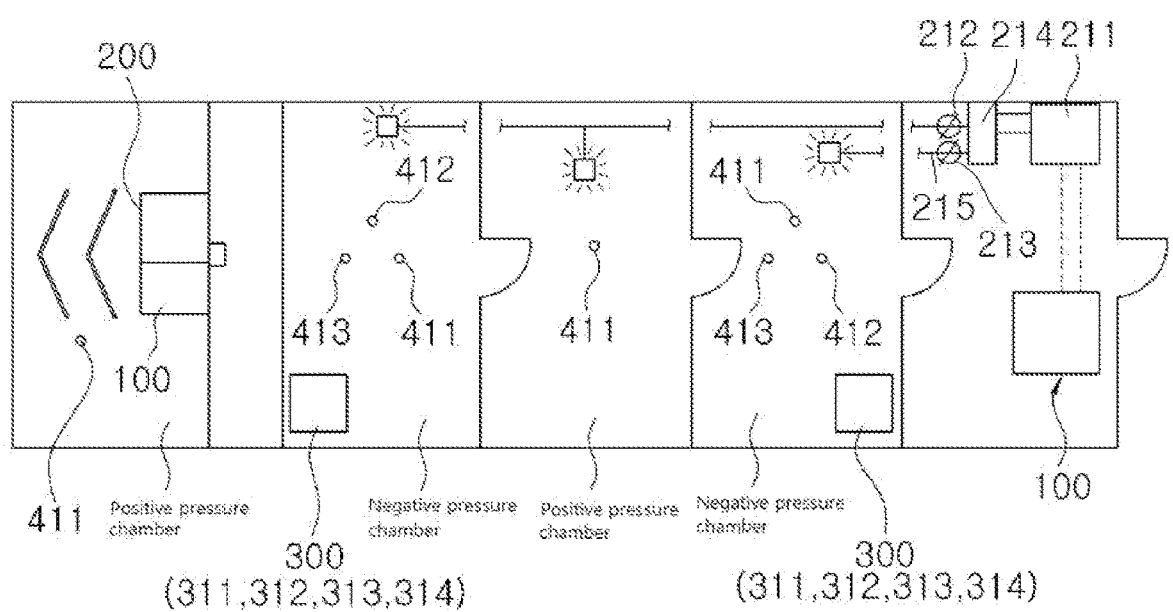
FIG. 10 is a partial sectional view showing a special-purpose vehicle, to which the positive pressure and negative pressure maintenance system according to a preferred embodiment of the present invention is applied.

FIG. 9 is an exemplary view showing a special-purpose vehicle, to which the positive pressure and negative pressure maintenance system according to a preferred embodiment of the present invention is applied, and FIG. 10 is a partial sectional view showing a special-purpose vehicle, to which the positive pressure and negative pressure maintenance system according to a preferred embodiment of the present invention is applied.

Referring to FIGS. 9 and 10, the present invention may be applied to a positive pressure and negative pressure system for special-purpose vehicles such as broadcasting relay vehicles, medical examination vehicles and emergency patient transport vehicles, educational promotion vehicles, chemical analysis vehicles, sampling vehicles, chemical, biological, and radiological (CBR) analysis vehicles, military communication vehicles, animal carcass collection and biological analysis vehicles, etc.

To describe with reference to the accompanying drawings, with regard to a positive pressure and negative pressure maintenance system having a bacteria sterilizing function and a harmful material and radioactive material removing function according to the present invention, in case of an analysis room and a driver's cabin, two positive pressure maintenance systems, which include the preprocessing unit 100, the air supply member 200, the postprocessing unit 300 and the control panel 400, may be installed therein, while one negative pressure maintenance system of the negative pressure chamber, which includes the air supply member 200, the postprocessing unit 300 and the control panel 400, may be installed therein as described above. The above positive pressure maintenance systems and the negative pressure maintenance system may be installed separately and independently from each other.

The positive pressure and negative pressure maintenance system for special-purpose vehicles may have the same configuration as that of the systems shown in FIGS. 1 to 8. In FIGS. 9 and 10, the preprocessing unit 100, the air supply member 200, the postprocessing unit 300 and the control panel 400 are indicated and the detailed configuration of each component 100, 200, 300 and 400 is too complicated to be indicated and thus omitted herein, and the present specification has been described with reference to the detailed configuration numbers.

An indoor pressure of the analysis room may be maintained at a pressure of 25 Pa or more, and an indoor pressure of the decontamination room, the sterilization room, the shower room, and the isolation room may be maintained at a negative pressure in the range of −2.5 to −11 Pa.

In addition, an indoor pressure in the driver's cabin may be maintained to be a pressure of 25 Pa or more.

Furthermore, the positive pressure and negative pressure maintenance system having a bacteria sterilizing function and a harmful material and radioactive material removing function according to the present invention may be installed at one side of an upper portion of or a rear surface of the driver's cabin, and may be installed in a separately divided mechanical room of a rear portion of a vehicle or at one side of a lower space of or at one side of an upper portion of the analysis room.

Moreover, a sampling vehicle may be a small-sized vehicle of SOLATI type, in which a driver's cabin and an analysis room may be combined into an open space, and thus the analysis room and the driver's cabin may be maintained at a positive pressure with one positive pressure equipment in the rear space of the vehicle.

Besides, an interior of a trailer (or an interior of a modified bus) of a special-purpose vehicle may have the positive pressure maintenance space and the negative pressure maintenance space, which may be divided according to a purpose of use. In case of a CBR analysis vehicle, a positive pressure may need to be maintained at 25 Pa or more. In case of a decontamination room, a negative pressure may need to be maintained (in the range of −2.5 Pa to −11.0 Pa). In case of an analysis room of an animal carcass collection and biological analysis vehicle, a negative pressure may need to be maintained in the range of −2.5 Pa to −11.0 Pa. In case of a fitting room, it is required that a positive pressure be maintained at 2.5 Pa or more, and the positive pressure and negative pressure maintenance systems be installed in a limited space inside the vehicle, and thus an available space may be limited.

The positive pressure and negative pressure maintenance system having a bacteria sterilizing function and a harmful material and radioactive material removing function for the special-purpose vehicle as described above, may include: a preprocessing unit 100, including: a first preprocessing member 110, which may be installed in one of three branch pipes connected to the main pipe, and may have a high-voltage discharge member 111 including a discharge electrode 11a, a ground electrode 111b and a high-voltage generator 111c inside a housing 101, as well as an adsorption member 112 including a grid 112a, a cage 112b, a DC power supply 112c, a conducting wire 112d and an adsorption material 112f loaded on a carrier 112e installed inside the housing 101, in which outside air may be introduced into the high-voltage discharge member 111 by a suction force of an air supply fan 211 of the air supply member 200 and may be subject to an electrochemical reaction such as dissociation, excitation, ionization, oxidation, reduction, etc. so as to decompose a covalent bond of contaminants such as ammonia (NH3), formaldehyde (HCHO), hydrogen fluoride (HF), etc., contained in air, resulting in dissociation into ions such as a hydrogen cation (H+), aldehyde (CHO—), fluorine ion (F+), etc., thereby adsorbing and removing harmful materials with an adsorption material 112f loaded on a porous carrier 112e; a second preprocessing member 120, which may be installed in another branch pipe, and which may include a first high-voltage discharge member 122 including a housing 121, a discharge electrode 122a and a ground electrode 122b which may be installed to face each other inside the housing 121, and a high-voltage generator 122c configured to supply high-voltage to electrodes 122a and 122b through a conducting wire, an adsorption member 123 including a grid 123a, a cage 123b, a DC power supply 123c, a conducting wire 123d and an adsorption material 123f loaded on a carrier 123e, and a second high-voltage discharge member 124 including a discharge electrode 124a and a ground electrode 124b which may be installed to face each other inside the housing while being spaced apart from the adsorption member 123, and a high-voltage generator 124c configured to supply high voltage to electrodes 124a and 124b through a conducting wire, in which outside air may be introduced into the first high-voltage discharge member 122 by a suction force of the air supply fan 211 of the air supply member 200 and may be subject to an electrochemical reaction such as dissociation, excitation, ionization, oxidation, reduction, etc. so as to decompose a covalent bond of contaminants such as ammonia (NH$_3$), formaldehyde (HCHO), hydrogen fluoride (HF), etc., contained in air, resulting in dissociation into ions such as a hydrogen cation (H+), aldehyde (CHO—), fluorine ion (F+), etc., thereby adsorbing and removing harmful materials with an adsorption material 123b loaded on a porous carrier 123c, and attacking a cellular wall of bacteria such as fungi, *Pseudomonas aeruginosa, Staphylococcus aureus*, pneumococcus, *Legionella*, etc., and floating viruses such as variant virus (MRSA), MERS coronavirus (MERS-COV), Ebola virus, Sascorona virus (SARS-COV), bacteria, etc., in the introduced air, with free radicals such as superoxide anion (O$_2$—), hydroxyl radical (OH-radical), nitrogen monoxide (NO), singlet oxygen ($^1$O$_2$), etc., including an active radical such as hydroxyl radical (OH-radical), in which an oxygen ion (O) generated in a process of second high-voltage discharge may be bonded with oxygen in an unstable form, resulting in decomposition and perforation of the cellular wall, damage to biological tissues and organs, and sterilization; and a third preprocessing member 130, which may be installed in one of three flow paths, and which may include: a high-voltage discharge member 131 including a discharge electrode 131a and a ground electrode 131b, which may be installed to face each other inside a housing, and a high-voltage generator 131c configured to supply high-voltage to electrodes 131a and 131b through a conducting wire, a hydrogen gas generator 132 including a housing 132a, a tap water supply pipe 132b, an electrolyte supply portion 132c, an alkali metal powder supply portion 132d, a first solenoid coil 132e, a second solenoid coil 132f, a fan 132g, an electromagnetic valve 132h, a heating coil 132i, and an injection nozzle 132j, a dehumidifying filter 134, and an electric adsorption portion 135 including ion exchange resin layers 135a and 135b, a discharge electrode 135c and a ground electrode 135d, a transformer 135e which decompresses the AC power of 220V, 60 Hz to the AC power of 60V to 100V, 60 Hz, a rectifier 135f with a built-in rectifier circuit which converts AC power to DC power, and a polarity converter 135g which converts a polarity of DC power supplied to the electrodes 135c and 135d at every time set to a tinier (not shown), in which outside air may be introduced into the high-voltage discharge member 131 by a suction force of an air supply fan 211 of the air supply member 200 and may be subject to an electrochemical reaction such as dissociation, excitation, ionization, oxidation, reduction, etc. so as to decompose a covalent bond of contaminants such as ammonia (NH3), formaldehyde (HCHO), hydrogen fluoride (HF), etc., contained in air, resulting in dissociation into ions such as a hydrogen cation (H+), aldehyde (CHO-), fluorine ion (F+), etc., after which the hydrogen gas produced from the hydrogen gas generator 132 may be injected into the dissociated outside air through a nozzle installed in a pipeline and mixed together, then dehumidified in a dehumidifying filter 134, and then transferred to the electric adsorption portion 135, so that DC power may be supplied to a discharge electrode 134c and a ground electrode 134d having ion exchange resin layers 135a and 135b coated on an outer surface thereof so as to start discharge between the discharge electrode 134c and the ground electrode 134d and activate metal ions of the ion exchange resin layers 135a and 135b, thereby carrying out an oxidation reaction with ion materials in the introduced outside air, while removing radioactive materials through a reduction reaction with a hydrogen cation (H+) produced by decomposing a hydrogen molecule during discharge; an air supply member 200, which includes an air supply fan 211, in which at least one fan selected from sirocco, airfoil, turbo and blower type fans may be installed at a distance apart from the preprocessing member 100 so as to pressurize outside air, and may be so configured that an air volume control damper 212 may be installed in a main pipe 214 connected to and branched off from a main pipe and connected with the positive pressure chamber so as to supply the air supplied by the air supply 211 fan into the positive pressure chamber, a circulation fan 221 may be installed in a circulation pipe to circulate a part of air of the positive pressure chamber into the preprocessing unit, and an air volume control damper 213 of the negative pressure chamber may be installed in a branch pipe 215 branched off from the main pipe 214 and connected to the negative pressure chamber so as to supply air into the negative pressure chamber; a postprocessing unit 300, which may include a first high-voltage discharge member 312, which may be installed at one side of an upper part of or one side of an upper part of a side surface of a negative pressure maintenance space, and may include a discharge fan 311 inside an independent housing 301, a discharge electrode 312a and a ground electrode 312b, which are installed to face each other inside the housing, and a high-voltage generator 312c, which supplies high voltage to the electrodes 312a and 312b through a conducting wire, an adsorption member 313 including a grid 313a, a cage 313b, a DC power supply 313c, a conducting wire 313d, and an adsorption material 313f; a second high-voltage discharge member 314 including a housing 301, a discharge electrode 314a and a ground electrode 314b, which are installed to face each other inside the housing, and a high-voltage generator 312c, which supplies high voltage to the electrodes 314a and 314b through a conducting wire, in which the control panel 400 may supply AC power to a discharge fan 313 and first and second high-voltage discharge members 312 and 314 so as to suction and pressurize a polluted indoor air in the negative pressure maintenance space and transfer the resulting air into the first high-voltage discharge portion 312 by using the discharge fan 313. If a high voltage generated from the high-voltage generator 312c is applied to the discharge electrode 312a and the ground electrode 312b through a conducting wire, a very high field electron energy band may be created to start discharge between two electrodes 312a and 312b.

The polluted air containing harmful chemicals, bacteria and viruses in the negative pressure chamber by a suction force of the discharge fan 311 may pass between the electrodes 312a and 312b, during which high field electron energy formed between the electrodes may be irradiated to the polluted air, so as to dissociate a covalent bond of chlorohexidine gluconate, which is an antiseptic for disinfecting hand and skin and disinfecting a surgical site, isopropyl alcohol, which is a hand sanitizer, and besetine solution (volatilized vapor), which is an antiseptic for torn wound, burn, ulcer and abscess, resulting in ionization. Then, the resulting air may be transferred to the adsorption member 313 and adsorbed to an adsorbing agent including at least one material selected from zeolite (ZSM-5, ZSM-8) mixed with globular conductive activated carbon, activated alumina mixed with conductive activated carbon, or pellet-type activated carbon and transferred to the second high-voltage discharge member 314.

If a high voltage generated from the high-voltage generator 314c is applied to the discharge electrode 314a and the ground electrode 314b through a conducting wire, a very high field electron energy band may be created between two electrodes 314a and 314b in the first high-voltage discharge member 312 and the resulting air may be purified in the first high-voltage discharge member 312 and the adsorption member 313 while passing through a discharge area, and then introduced into the second high-voltage discharge member 314, thereby attacking a cellular wall of bacteria such as fungi, Pseudomonas aeruginosa, Staphylococcus aureus, pneumococcus, Legionella, etc., and floating viruses such as variant virus (MRSA), MERS coronavirus (MERS-COV), Ebola virus, Sascorona virus (SARS-COV), bacteria, etc., in the introduced air, with free radicals such as superoxide anion ($O_2-$), hydroxyl radical (OH-radical), nitrogen monoxide (NO), singlet oxygen ($^1O_2$), etc., including an active radical such as hydroxyl radical (OH-radical), in which an oxygen ion (O) generated by dissociating an oxygen molecule ($O_2$), a nitrogen molecule ($N_2$) and a water molecule ($H_2O$) of water vapor, which are introduced into the second high-voltage discharge member 314, may be bonded with oxygen in an unstable form, resulting in decomposition and perforation of the cellular wall, damage to biological tissues and organs, and sterilization of bacteria and floating viruses, thereby discharging the sterilized air to block a path of spreading infectious bacteria and viruses with air as a medium. The positive pressure and negative pressure maintenance system having a bacteria sterilizing function and a harmful material and radioactive material removing function for the special-purpose vehicle as described above may further include the control panel 400, which may perform a control by supplying power to or cutting off power from the preprocessing unit 100, the air supply member 200, and the postprocessing unit 300 by a control program, which is programmed and inputted in advance according to data on a pressure and a concentration of harmful materials measured in real time by detection sensors 411 and 412 installed in a space in which the positive pressure and the negative pressure are to be maintained.

In addition, the control panel 400 of the postprocessing unit 300 may be separately and independently installed, or the control panel 400 of the positive pressure maintenance system may be used.

Furthermore, with regard to the discharge fan 311 and the air volume control damper (not shown), the control panel 400 may adjust a number of rotations (RPM) of the discharge fan 311 and an opening rate of the air volume control damper (not shown) and adjust an indoor pressure of the positive and negative pressure chambers within the range of set pressure by a control circuit which is programmed and inputted in advance according to data on an indoor pressure which is measured and transmitted in real time by detection sensors 411 and 412 installed in the positive pressure chamber and the negative pressure chamber. If the indoor pressure fails to reach or exceeds the range of set pressure, the control panel may sound a warning alarm so that an occupant may take a manual measure.

Moreover, in order to confirm if the indoor pressure of the positive pressure chamber and the negative pressure chamber are properly maintained, the detection sensor 412 and a differential pressure gauge for measuring a differential pressure inside and outside the room may be installed, respectively, so as to compare and measure an indoor pressure value displayed on the monitor of the control panel with an indicated pressure value of the differential pressure gauge.

Besides, the air supply and discharge fans 211 and 311 may include any one fan selected from a multi-blade fan (SIROCCO FAN), an airfoil fan (AIRFOIL FAN) and a turbo fan (TURBO FAN), in which the multi-blade fan (SIROCCO FAN) may be applied to a space in which a positive pressure is to be maintained at 2.5 Pa to 8.0 Pa, or may be used in a space in which a negative pressure is to be maintained at −2.5 Pa to −11.0 Pa, and the airfoil fan (AIRFOIL FAN) or the turbo fan (TURBO FAN) may be applied to a space in which a positive pressure is to be maintained at 25 Pa to 250 Pa.

In addition, if the air supply fan 211 and the air volume control dampers 212 and 213 of the air supply member as well as the discharge fan 321 of the postprocessing unit 300 are installed in explosion hazardous areas of "Class 0", "Class 1", and "Class 2", where an explosive atmosphere is created due to combustible gases, etc., a motor of the fans 211 and 321 and the air volume control damper 212 and 213 may cause a spark from a brush portion and a contact portion when starting or stopping the positive pressure and negative pressure maintenance system and this spark may serve as a source of ignition among fire and explosion factors, and thus the motor may be formed by selecting at least one of an explosion-proof structure for internal pressure (d, flame-proof enclosure), an increased safety explosion-proof structure (e, increased safety), an intrinsic safety explosion-proof structure (i, intrinsic safety), and a pressurization explosion-proof structure (p, pressurization).

Furthermore, a motor of the fans 211 and 321 and the air volume control dampers 212 and 213, which may be installed in places classified as "Class 20", "Class 21", and "Class 22" where an explosive atmosphere is created due to combustible dusts, etc., may be formed by selecting at least one suitable explosion-proof structure out of "dust explosion-proof structure for internal pressure (tD)," "dust mold explosion-proof structure (mD)," "dust intrinsic safety explosion-proof structure (iD)," and "dust pressure explosion-proof structure (pD)."

Moreover, a material of a casing of the fans 211 and 321 may have a non-spark material performance in such a way that any one material may be selected from non-spark materials such as PVC, FRP (glass fiber molding foam), carbon fiber molding foam, etc., one material of a blade of the fans 211 and 321 may be selected from copper or copper alloy, duralumin or aluminum alloy, and the FRP may be coated by a certain thickness or more on a surface of steel and stainless steel (STS304).

The reason for selecting and adopting the non-spark material for the casing and the blade of the fans 211 and 321 described above may be that, if a bearing inserted into a rotational shaft is worn and damaged, a blade rotating in connection with the rotational shaft inside the casing may break away due to the damaged bearing or may collide with an interior of the casing and cause a scratch phenomenon due to an abnormal rotation, and may cause a spark in case of a general metal material. Then, if inflammable gas, combustible gas and combustible dust exceeding an explosion lower limit are introduced into the casing of the fans 211 and 321, the spark caused by the collision and the scratch phenomenon may serve as a source of ignition. Thus, the casing and the blade may be made of the non-spark material in order to prevent any fire and explosion.

As described above, the positive pressure and negative pressure maintenance system of the present invention may include the preprocessing unit, the air supply member, the postprocessing unit and the control panel, in which the first preprocessing member of the preprocessing unit, including the high-voltage discharge member and the adsorption portion, may remove harmful materials through an electrochemical reaction and an adsorption process, in which the second preprocessing member of the preprocessing unit, including the first high-voltage discharge member, the adsorption portion and the second discharge member, as well as the first high-voltage discharge member and the adsorption portion may remove harmful materials through an electrochemical reaction and an adsorption process, in which the second high-voltage discharge member may sterilize bacteria and floating viruses with free radicals such as superoxide anion ($O_2{-}$), hydroxyl radical (OH-radical), nitrogen monoxide (NO), singlet oxygen ($^1O_2$), etc., which are generated by dissociating the constituent molecules of purified, in which the third preprocessing member of the preprocessing unit, including the high-voltage discharge member, the hydrogen gas generator and the electric adsorption portion may remove general harmful materials and activate radioactive materials through an electrochemical reaction, may mix the hydrogen gas produced from the hydrogen gas generator with the polluted air having harmful materials removed and radioactive materials activated, may adsorb the radioactive materials through the ion exchange resin layer coated on an outer surface of the electrodes of the electric adsorption portion, and may supply high-voltage DC power to the electrodes to protonate the hydrogen gas and remove the radioactive materials through a reduction reaction, in which at least one of the first, second and third preprocessing members may be selected and applied to sites in a customized way, in which an indoor pressure may be detected and measured in real time by a pressure detection sensor installed in the positive pressure chamber and the negative pressure chamber and may be transmitted to the control panel, so as to adjust a number of revolutions (RPM) of fan of the air supply member, according to a control circuit, which is programmed and inputted in advance, and adjust an opening rate of the air volume control damper, thereby adjusting an indoor pressure within the range of set values, and in which the postprocessing unit including the discharge fan, the high-voltage discharge member and the adsorption member may sterilize bacteria and floating viruses and dissociate harmful materials with free radicals such as superoxide anion ($O_2{-}$), hydroxyl radical (OH-radical), nitrogen monoxide (NO), singlet oxygen ($^1O_2$), etc. generated by dissociating the constituent molecules of the polluted air in a decontamination room and a genetically modified biology laboratory and analysis room through an electrochemical reaction of the high-voltage discharge member, after which the adsorption member may adsorb the harmful materials to remove the same and discharge the resulting air into the outside air, thereby blocking a path of bacteria and viruses with air as a medium. In addition, the positive pressure and negative pressure maintenance system having the configuration as described above may be applied to special-purpose vehicles and government dissipation facilities.

Although the preferred embodiments of the present invention have been described in detail above, the present invention is not limited to the specific preferred embodiments described above, and those skilled in the art to which the present invention belongs may implement various modifications without departing from the gist of the present invention, and such modifications are within the scope of the claims.

LIST OF REFERENCE NUMBERS

100: Preprocessing unit
110: First preprocessing member, 101: Housing

111: High-voltage discharge member, 11a: Discharge electrode
111b: Ground electrode, 111c: High-voltage generator
112: Adsorption member, 112a: Grid
112b: Cage, 112c: DC power supply
112d: Conducting wire, 112e: Carrier
112f: Adsorption material
120: Second preprocessing member, 121: Housing
122: First high-voltage discharge member, 122a: Discharge electrode
122b: Ground electrode, 122c: High-voltage generator
122d: Conducting wire
123: Adsorption member, 123a: Grid
123b: Cage, 123c: DC power supply
123d: Conducting wire, 123e: Carrier
123f: Adsorption material
124: Second high-voltage discharge member, 124a: Discharge electrode
124b: Ground electrode, 124c: High-voltage generator
130: Third preprocessing member, 131: High-voltage discharge member
131a: Discharge electrode, 131b: Ground electrode
131c: High-voltage generator
132: Hydrogen gas generator, 132a: Housing
132b: Tap water supply pipe, 132c: Electrolyte supply portion
132d: Alkali metal powder supply portion, 132e: First solenoid coil
132f: Second solenoid coil, 132g: FAN
132h: Electromagnetic valve, 132i: Heating coil
132j: Spray nozzle, 132k: Hydrogen gas bombe
132l: Pressure reducer, 132m: Flow control valve
132n: Supply pipe
134: Dehumidifying filter, 134a: Cage
134b: Dehumidifying agent
135: Electric adsorption portion, 135a: Ion exchange resin layer
135b: Ion exchange resin layer, 135c: Discharge electrode
135d: Ground electrode, 135e: Transformer
135f: Rectifier, 135g: Polarity converter
200: air supply member
211: Air supply fan, 212: Positive pressure chamber air volume control damper
213: Negative pressure chamber air volume control damper,
214: Main pipe
221: Circulating fan
300: Postprocessing unit
301: Housing, 311: Discharge fan
312: First high-voltage discharge member, 312a: Discharge electrode
312b: Ground electrode, 312c: High-voltage generator
313: Adsorption member, 313a: Grid
313b: Cage, 313c: DC power supply
313d: Conducting wire, 313e: Adsorption material
314: Second high-voltage discharge member, 314a: Discharge electrode
314b: Ground electrode, 314c: High-voltage generator
400: Control panel
411: Positive pressure chamber detection sensor, 412: Negative pressure chamber detection sensor
413: Harmful gas concentration detection sensor

The invention claimed is:

1. A positive pressure and negative pressure maintenance system having a bacteria sterilizing function and a harmful material and radioactive material removing function and installed inside a building including a special-purpose vehicle, the system comprising:
a preprocessing unit configured to select and use at least one of a first preprocessing member installed in one branch pipe of three branch pipes connected to a main pipe so as to purify polluted air, a second preprocessing member installed in another branch pipe so as to sterilize bacteria and variant viruses in air, and a third preprocessing member installed in still another branch pipe so as to remove radioactive materials;
an air supply member installed at a distance from the preprocessing unit so as to supply air into a positive pressure chamber and a negative pressure chamber; a postprocessing unit installed at one side of an upper part of or one side of an upper part of a side surface of the negative pressure chamber so as to sterilize bacteria and floating viruses in polluted air and discharge a resulting air to an outside; and
a control panel configured to perform a control by supplying power to or cutting off power from the preprocessing unit, the air supply member, and the postprocessing unit by a control program, which is programmed and inputted in advance according to data on a pressure and a concentration of harmful materials measured in real time by a detection sensor installed in a space in which a positive pressure and a negative pressure are to be maintained.

2. The system of claim 1, wherein the first preprocessing member comprises a high-voltage discharge member and an adsorption member inside a housing, so that the polluted air containing harmful materials is ionized with a covalent bond of a harmful material molecule dissociated in a process of high-voltage discharge and is then adsorbed onto an adsorption material loaded on a carrier of an adsorption member so as to purify the polluted air.

3. The system of claim 1, wherein the second preprocessing member comprises a first high-voltage discharge member, an adsorption member and a second high-voltage discharge member inside a housing, so that the polluted air containing harmful materials is ionized with a covalent bond of a harmful material molecule dissociated in a process of high-voltage discharge and is then adsorbed onto an adsorption material loaded on a carrier of the adsorption member so as to purify the polluted air, and then to sterilize bacteria and variant viruses in air, which are introduced, with free radicals including superoxide anion ($O_2^-$), hydroxyl radical (OH-radical), nitrogen monoxide (NO), singlet oxygen ($^1O_2$), in which an oxygen ion (O) generated by dissociating a covalent bond of nitrogen ($N_2$), oxygen ($O_2$) and a water molecule ($H_2O$) of water vapor, which are constituent materials of purified air, is bonded with oxygen in an unstable form.

4. The system of claim 1, wherein the third preprocessing member comprises a high-voltage discharge member, a hydrogen gas generator, and an electric adsorption portion and is so configured that the polluted air containing radioactive materials is ionized by dissociating a covalent bond of a harmful material molecule in a process of high-voltage discharge, a hydrogen gas generated from a hydrogen generator is injected into a resulting ionized air and mixed together, and an air containing radioactive materials mixed with hydrogen has the radioactive materials adsorbed onto an ion exchange resin layer coated onto an outer surface of a discharge electrode and a ground electrode of the electric adsorption portion, while high voltage is applied to the discharge electrode and the ground electrode at the same time, so that the radioactive materials on the ion exchange resin layer are activated and adsorbed onto the resin layer with a hydrogen molecule dissociated into a hydrogen cation, thereby removing the radioactive materials through a reduction reaction of the radioactive materials in association with the hydrogen cation and an activated metal ion of the ion exchange resin layer.

5. The system of claim 1, wherein the air supply member comprises an air supply fan, in which at least one fan selected from sirocco, airfoil, turbo and blower type fans is installed to pressurize outside air, and an air volume control damper which is installed in the branch pipe connected to and branched off from the main pipe and connected with the positive pressure chamber so as to supply the air supplied by the air supply fan into the positive pressure chamber and which is also installed in the branch pipe branched off from the main pipe and connected to the negative pressure chamber.

6. The system of claim 1, wherein the postprocessing unit has a fan and a high-voltage discharge member installed inside an independent housing, so as to suction and pressurize a polluted indoor air of a space in which a negative pressure is to be maintained and supply a resulting air into the high-voltage discharge member by using the fan, thereby sterilizing bacteria and floating viruses in the polluted air with free radicals including superoxide anion ($O_2$-) hydroxyl radical (OH-radical), nitrogen monoxide (NO), singlet oxygen ($^1O_2$) in which an oxygen ion (O) generated in a process of high-voltage discharge is bonded with oxygen in an unstable form.

7. The system of claim 2, wherein the high-voltage discharge member of the first preprocessing member of the preprocessing unit comprises a discharge electrode, a ground electrode, a high-voltage generator, and a conducting wire, in which the adsorption member includes a grid, a cage, a DC power supply, a conducting wire and an adsorption material loaded on a carrier, so as to primarily remove harmful materials from the air containing the harmful materials, which is introduced to the high-voltage discharge member, through an electrochemical reaction including dissociation, ionization, excitation, oxidation, reduction reaction in a process of high-voltage discharge and then adsorb and remove surplus harmful materials in a primarily purified air with the adsorption material loaded on the carrier of the adsorption member.

8. The system of claim 7, wherein the adsorption member has the carrier and the adsorption material installed therein, in which the carrier for adsorbing acid gas including hydrogen chloride (Hcl), chlorine ($Cl_2$), sulfur dioxide ($SO_2$), hydrogen sulfide ($H_2H$), is activated carbon, in which an adsorbing agent loaded on the carrier includes at least one selected from iron sulfate, ammonium iron sulfate, iron oxide, iron nitrate, iron hydroxide, and iron chloride, and at least one selected from zinc sulfate, ammonium zinc sulfate, zinc oxide, zinc hydroxide, zinc nitrate, and zinc chloride, so that the adsorption material where the ion compound and the zinc chloride material are mixed is loaded on an activated carbon carrier, in which the carrier for adsorbing hydrogen fluoride (HF) gas includes at least one material selected from porous polymers including styrene-based polymer, acryl-based polymer, methacryl-based polymer, vinyl-based polymer, and urethane-based polymer, in which the adsorption material includes at least one material selected from ethylamine, butylamine hexylamine, octylamine, decylamine, dodecylamine, tetradecylamine, hexadecylamine, octadecylamine, ethylenediamine, tetramethylenediamine, and hexamethylenediamine and is loaded on the porous carrier, and in which an adsorption material of formaldehyde, acetaldehyde, toluene, xylene, paradichlorobenzene, ethylbenzene, styrene, chlorpyrifos, di-n-butyl phthalate, di-2-ethylhexyl tetradecane phthalate, diazinone, fenobucarb, and volatile organic compound (VOCs) materials, includes at least one material selected from globular zeolite (ZSM-5, ZSM-8), activated alumina or pellet-type activated carbon and is filled into a case without a separate carrier.

9. The system of claim 3, wherein the second preprocessing member comprises the first high-voltage discharge member, the adsorption member and the second high-voltage discharge member, in which the first high-voltage discharge member includes a discharge electrode, a ground electrode, a high-voltage generator, and a conducting wire, in which the adsorption member includes a grid, a cage, a DC power supply, a conducting wire and an adsorption material loaded on a carrier, and in which the second high-voltage discharge member includes a discharge electrode, a ground electrode and a high-voltage generator for supplying high voltage to the electrodes through a conducting wire, so as to primarily purify an air containing contaminants, which is introduced to the first high-voltage discharge member, through an electrochemical reaction including dissociation, ionization, excitation, oxidation, reduction reaction, in a process of high-voltage discharge, adsorb and remove surplus contaminants in a primarily purified air with the adsorption material loaded on the carrier of the adsorption member, and sterilize bacteria and floating viruses in air, which is introduced, with free radicals including superoxide anion ($O_2$-), hydroxyl radical (OH-radical), nitrogen monoxide (NO), singlet oxygen ($^1O_2$), in which an oxygen ion (O) generated by dissociating a covalent bond of nitrogen ($N_2$), oxygen ($O_2$) and a water molecule ($H_2O$) of water vapor, which are constituent materials of air purified by the second high-voltage discharge member, is bonded with oxygen in an unstable form.

10. The system of claim 8, wherein the adsorption member of the first preprocessing member comprises a grid, a cage, a DC power supply, a conducting wire, and an adsorption material loaded on a carrier, and the adsorption member of the second preprocessing member comprises a grid, a cage, a DC power supply, a conducting wire and an adsorption material loaded on a carrier, in which a negative pole of the DC power supply is connected to the grid and a positive pole of the DC power supply is connected to the cage, so that attractive force works between the cage and the carrier filled inside the cage, thereby enhancing an adsorption rate of harmful materials.

11. The system of claim 4, wherein the third preprocessing member comprises the high-voltage discharge member including the discharge electrode, the ground electrode and a high-voltage generator configured to supply high voltage to the electrodes through a conducting wire, the hydrogen gas generator including a housing, a tap water supply pipe, an electrolyte supply portion, an alkali metal power supply portion, a first solenoid coil, a second solenoid coil, a fan, an electromagnetic valve, a heating coil and an injection nozzle, or including a hydrogen gas bombe, a pressure reducer, a flow control valve and a supply pipe, and the electric adsorption portion including a dehumidifying filter having a housing and a dehumidifying agent, the ion exchange resin layer, the discharge electrode and the ground electrode having the ion exchange resin layer coated on an outer surface thereof, and a high-voltage generator.

12. The system of claim 11, wherein the electrolyte supply portion comprises a storage container, a supply pipe and an electromagnetic valve, in which an electrolyte stored in the storage container includes at least one material selected from the group consisting of potassium chloride, sodium chloride, calcium chloride, lithium chloride, potassium nitrate, sodium nitrate, potassium sulfate and a mixture thereof, and is stored in the storage container and then used.

13. The system of claim 12, wherein the alkali metal powder supply portion comprises a storage container, a supply pipe, and an electromagnetic valve, in which at least one material selected from magnesium, lithium, sodium, and potassium is stored in the storage container and then used.

14. The system of claim 13, wherein the first solenoid coil has a coil with a predetermined diameter wound around one side portion of an outer surface of the housing, and has a coil with a predetermined diameter wound by a predetermined number of turns around one side of an outside of a rod having a predetermined diameter and a predetermined length, which is installed in an inner center of the housing, and the second solenoid coil is installed at a distance apart from an inner surface of the housing and the first solenoid coil installed in a center of the housing, in which winding directions of the first solenoid coil and the second solenoid coil are opposite to each other, in which a mixed solution of tap water, electrolyte and alkali metal power inside the housing flows by a magnetic field and Lorentz's force respectively in a direction perpendicular to a direction of electric current flow of the first and second solenoid coils so as to increase an amount of hydrogen generated, and in which power is supplied to the first and second solenoid coils having coils wound in directions opposite to each other, so that magnetic fields generated in a direction vertical to a direction of electric current flow are generated in directions opposite to each other, and thus zero-field (SE) energy generated by superimposed magnetic fields more activates the mixed solution of tap water, electrolyte and alkali metal powder, thereby increasing an amount of hydrogen generated.

15. The system of claim 5, wherein the radioactive materials and the hydrogen gas are introduced into the third preprocessing member by a suction force of the air supply fan of the air supply member, so that the radioactive materials are adsorbed onto the ion exchange resin layer coated on an outer surface of the discharge electrode and the ground electrode and are subject to a first oxidation reaction with a functional group contained in resin, and the hydrogen gas dissociates into a hydrogen atom (H) between the discharge electrode and the ground electrode so as to remove the reactive materials including lead isotope ($^{210}$Ra), cesium (CS), uranium isotope ($^{234,238}$U), thorium isotope ($^{230}$Th), radium isotope ($^{226}$Ra), radon isotope ($^{222}$Rn), polonium isotope ($^{210,218}$Po), lead (Pb) isotope ($^{210}$Pb) through a reduction reaction.

16. The system of claim 5, wherein an indoor pressure control of the positive pressure chamber and the negative pressure chamber is performed by at least one method selected from a method, in which an indoor pressure is detected by each detection sensor installed indoors and transmitted to a control panel, so as to adjust a number of rotations (RPM) of the fan, which supplies, circulates and discharges air into the positive pressure chamber and the negative pressure chamber, according to a control circuit, which is programmed and inputted in advance, thereby adjusting an air volume to be supplied and discharged into the positive pressure chamber and the negative pressure chamber, or a method in which an opening rate of the air volume control damper installed in an air supply, discharge and circulation pipeline is adjusted or an operator checks an indicated value of a differential pressure gauge installed in the positive pressure chamber and the negative pressure chamber, so as to adjust an opening rate of the damper installed in the air supply, discharge and circulation pipeline, so that the control panel sounds an alarm when an indoor pressure is less than or more than a set value and automatically adjusts the number of rotations (RPM) of fans and an opening rate of the air volume control damper, thereby maintaining the indoor pressure within a set range.

* * * * *